United States Patent [19]

Konetschny-Rapp et al.

[11] Patent Number: 5,856,309
[45] Date of Patent: Jan. 5, 1999

[54] AMIDINOPYRROLINE DERIVATIVES, PROCESSES FOR THEIR PRODUCTION AND PHARMACEUTICAL AGENTS CONTAINING THESE COMPOUNDS

[75] Inventors: Silvia Konetschny-Rapp, Heddesheim; Hans-Willi Krell, Penzberg; Ulrich Martin, München; Richard Engh, Wessling; Christos Tsaklakidis, Weinheim, all of Germany

[73] Assignee: Boehringer Mannheim GmbH, Mannheim, Germany

[21] Appl. No.: 843,209

[22] Filed: Apr. 14, 1997

Related U.S. Application Data

[63] Continuation-in-part of PCT/EP95/03982 Oct. 10, 1995 and continuation-in-part of PCT/EP96/05494 Dec. 9, 1996.
[51] Int. Cl.$^6$ .......................... A61K 38/00; A61K 38/04; C07D 207/18; C07D 403/00
[52] U.S. Cl. .......................... 514/18; 514/212; 514/313; 514/315; 514/408; 540/602; 530/330; 530/331; 546/159; 546/208; 548/565; 548/569
[58] Field of Search ..................... 548/565, 569; 514/408, 18, 212, 313, 315; 540/602; 546/159, 208; 530/330, 331

[56] References Cited

U.S. PATENT DOCUMENTS 5,296,494  3/1994  Lavielle et al. ........................... 548/565
5,300,508  4/1994  Valla et al. ............................... 548/565

Primary Examiner—Johann Richter
Assistant Examiner—Joseph Murray
Attorney, Agent, or Firm—Nikaido, Marmelstein, Murray & Oram LLP

[57] ABSTRACT

Compound of formula (I) are disclosed

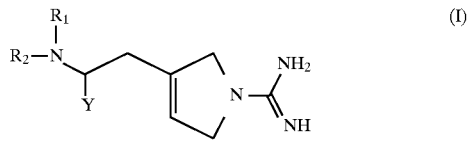

as well as optically active isomers or pharmacologically acceptable salts thereof. The compounds are useful active ingredients in pharmaceutical compositions, and methods of treating osteoporosis, inflammation or diseases which are due to thromboembolic events. Compounds of formula (II) are also disclosed

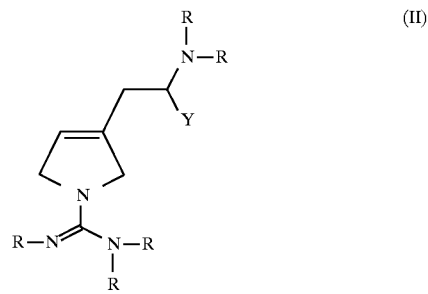

which are useful as starting compounds for preparing compounds of formula (I).

17 Claims, No Drawings

AMIDINOPYRROLINE DERIVATIVES, PROCESSES FOR THEIR PRODUCTION AND PHARMACEUTICAL AGENTS CONTAINING THESE COMPOUNDS

CROSS REFERENCE TO RELATED APPLICATION

This application is a continuation-in-part of International Application PCT/EP95/03982, filed Oct. 10, 1995, and a continuation-in-part of PCT/EP96/05494 filed Dec. 9, 1996 and designating the U.S.

BACKGROUND OF THE INVENTION

The present invention concerns new amidinopyrroline derivatives, processes for their production and their use thereof in pharmaceutical preparations.

SUMMARY OF THE INVENTION

It was found that compounds of the general formula (I) have the properties of an arginine mimetic. Arginine mimetics are pharmacophores which can replace arginine or an arginyl residue for example in inhibitors. Derivatives of (I) can replace arginine or already known arginine mimetics in biologically active substances and especially in therapeutically active substances. In particular they can be used in inhibitors for serine proteases such as thrombin or trypsin inhibitors. Inhibitors of thrombin inhibit the thrombin induced coagulation of fibrinogen in blood as well as the thrombin induced aggregation of blood platelets. Thus they prevent the formation of coagulation thrombi and platelet-rich thrombi and can be used to treat and prevent diseases such as thromboses, apoplexy, cardiac infarction, inflammations and arteriosclerosis.

Thrombin the last enzyme of the coagulation cascade cleaves fibrinogen to fibrin which is cross-linked by factor XIII and becomes an insoluble gel which forms the matrix for a thrombus. Thrombin activates platelet aggregation by proteolysis of its receptor on the blood platelets and in this manner also contributes to thrombus formation. When blood vessels are damaged these processes are necessary to stop bleeding. Under normal circumstances no measurable thrombin concentrations in blood plasma are present. An increase of the thrombin concentration can lead to the formation of thrombi and thus to thromboembolic diseases which occur very frequently above all in industrial countries. Thrombin is kept ready in the plasma in the form of prothrombin and is released from this by factor Xa. Thrombin activates factors V, VIII and XI which then convert factor X into Xa. By this means thrombin catalyses its own release which is why very rapid increases in thrombin concentrations can occur. Thrombin inhibitors and factor Xa inhibitors can therefore inhibit the release of thrombin, and the platelet induced and plasmatic blood coagulation.

Trypsin is a digestive enzyme which is excreted by the pancreas when required. When the pancreas is damaged or inflamed the trypsin release which this causes can lead to tissue destruction. Trypsin inhibitors can reduce this threat and be used for instance to treat pancreatitis.

In addition such arginine mimetics can be incorporated into active substances which are able to inhibit the binding of ligands that bind to their receptor via sequences containing RGD. RGD stands for the tripeptide Arg-Gly-Asp. Such ligands are for example fibrinogen, vitronectin or fibronectin. Such active substances can be used to treat diseases which are due to thrombo-embolic events such as stroke, myocardial infarction or arterial occlusive diseases as well as inflammations, osteoporosis or tumour diseases.

The invention concerns compounds which contain the structural element I as a pharmacophore as well as modifications known to a person skilled in the art which can be derived from the parent substance of structure I,

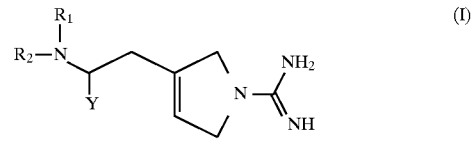

in which $R_1$, $R_2$ and Y can be the same or different and denote hydrogen or an organic residue. Preferred organic residues are such which result in a biological active compound of general formula I. Biological active means inter alia substances for plant protection and preferred pharmacological active compounds. Prodrugs of such biological active compounds are also included in the preferred structures of formula I. Prodrugs are substances which will be metabolized in vivo into the biological active compound. An example, but not a limitation for prodrugs are esters which will be converted to free acids by the organism, e.g. by the liver metabolism.

Especially preferred are such derivates of compounds of the general formula I, wherein an arginine substructure or a known arginine mimetic substructure in a biological active sustance is substituted by the backbone structure of formula I' or I".

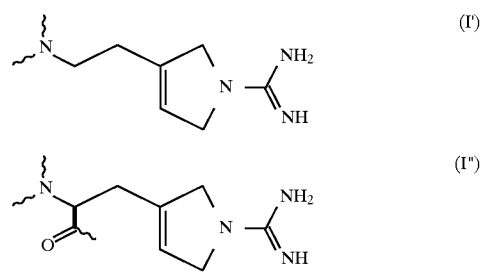

wherein the jagged bonds represent in said biological active compound the positions of the optional chemical bonds of the arginine or known arginine mimetic substructure which is substituted by the arginine mimetic structure (I') or (I") of the invention.

A collection of pharmacological active compounds can be found in data bases for INNs (International Nonproprietary Names) which are hereby incorporated by reference.

In this particular embodiment of the invention, particular compounds of the general formula (I) are preferred in which $R_1$ and/or $R_2$ denote hydrogen, an amino acid, peptidyl, alkylsufonyl or arylsulfonyl residue, Y denotes hydrogen or a residue of the formula COX, where X denotes hydrogen or an $OR_3$ or $NR_1R_2$ residue, where $R_3$ denotes hydrogen or C1–C6 alkyl such as methyl, ethyl, propyl or butyl preferably ethyl and $R_1$ and $R_2$ can be the same or different and have the meanings of the residues $R_1$ and $R_2$ denoted above.

The term "amino acid residue" denotes the residue of a natural or unnatural amino acid. Unnatural amino acids are understood as α-, β-, γ-and ω-aminocarboxylic acids as well as derivatives thereof. Derivatives are in particular understood as compounds which are alkylated on the amino group or the carboxy group. Derivatives are also included which are either decarboxylated or deaminated.

Examples of such amino acids and derivatives thereof are stated in the examples and preferred compounds. In particular these are D-amino acids, citrulline, homocysteine, homoserine, hydroxyproline, hydroxylysine, ornithine, sarcosine, tranexamic acid, Adc [3-(2-aminoethyl)-2,5 dihydropyrrol-1-yl]-carbamidine], Ada [(1-amidino-2,5-dihydro-1H-pyrrol-3-yl)-alanine], Cha [cyclohexyl-alanine], Choi [2-carboxy-6-hydroxy-octahydroindol], norLeu(cyclo)-Gly [3-amino-2-oxo-hexahydro-1-azepineacetic acid], Pcs [4-piperidine carboxylic acid], Pip [pipecolic acid], Pla [phenyllactic acid], N-Me-Phe, HOOCCH2-Phe, HOOCCH2-Cha, 1-carboxy-perhydroisoquinoline, N-cyclopentylglycine, EtSO2-Phe and N-(BuSO2-NorLeu(cyclo)-Gly.

A peptidyl residue is understood as a residue composed of any desired number of natural or unnatural identical of different amino acids. Peptidyl residues with 1–50 amino acids are preferred and those with 1, 2, 3 or 4 amino acids are particularly preferred.

Alkyl usually denotes a linear or branched alkyl residue with one to six carbon atoms. Aryl usually denotes a carbocycle with 6 to 14 C atoms or a 5- or 6-membered heterocycle with 1, 2 or 3 heteroatoms selected from O, N or S. Unsubstituted or optionally substituted phenyl or naphthyl residues are preferred.

The invention also concerns compounds of formula I

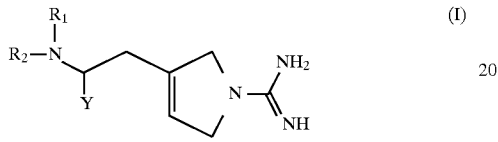

in which $R_1$, $R_2$ and Y are the same or different and are each independently selected from the group consisting of:

(1) hydrogen;

(2) C1–C6 alkyl which is unsubstituted or substituted with phenyl which is unsubstituted or substituted with O—(C1–C6 alkyl) which is unsubstituted or substituted by a 5- or 6-membered heterocyclic ring having 1–2 heteroatoms and having 1–2 substituents which is unsubstituted or has 1–2 substituents each independently selected from the group consisting of =O and (C1–C6 alkyl)—C(=O)—OH;

(3) a 5- or 6-membered heterocyclic ring having 1–2 heteroatoms which is unsubstituted or substituted with
 (A) (C1–C6 alkyl)—C(=O)-phenyl which is unsubstituted or substituted in the phenyl with 1–2O—(C1–C6 alkyl)—C(=O)—OH groups, or
 (B) a 5- or 6-membered heterocyclic ring having 1–2 heteroatoms which is unsubstituted or substituted with (C1–C6 alkyl)—C(=O)—OH;

(4) a 5- or 6- membered carbocyclic ring which is unsubstituted or substituted with (C1–C6 alkyl)—C(=O)—OH; and (5) —V—C(=O)—X where V is a chemical bond or C1–C6 alkyl and X is selected from the group consisting of
 (A) C1–C6 alkyl which is unsubstituted or substituted 1–2 times by
  (i) N(—$R_3$)—$R_4$, where $R_3$ and $R_4$ are each independently selected from the group consisting of hydrogen, a 5- or 6-membered carbocyclic ring and C(=O)—$R_5$ where $R_5$ is selected from the group consisting of (1) C1–C6 alkyl which is unsubstituted or has 1–2 substituents selected from the group consisting of phenyl, N(—H)—(C1–C6 alkyl) and N(—H)-(sulfonyl C1–C6 alkyl) and (2) a 1–2 ring heterocycle having 1–3 heteroatoms, or $R_3$ and $R_4$, together with the N atom to which they are attached, form a 5–7 membered heterocyclic ring which is unsubstituted or has 1–2 substituents each independently selected from the group consisting of =O, N(—H)—(C1–C6 alkyl) and N(—H)-(sulfonyl C1–C6 alkyl),
  (ii) C(=O)—N(—H)—(C1–C6 alkyl) where the alkyl is unsubstituted or has 1–3 substitutents each independently selected from the group consisting of C1–C6 alkyl, =O, —OH, phenyl, a 5- or 6-membered heterocyclic ring having 1–2 heteroatoms, and ≡CH, or
  (iii) a 5- or 6-membered carbocyclic ring (B) a 5- or 6-membered heterocyclic ring having 1–2 heteroatoms and which is unsubstituted or has 1–2 C1–C6 alkyl substituents each of which is unsubstituted or substituted with 1–3 substituents each independently selected from the group consisting of =O, —OH, —O—CH3, a 5- or 6-membered carbocyclic ring, a 1–2 ringed heterocyclic ring having 1–3 heteroatoms and N(—H)—(C1–C6 alkyl) where the alkyl is unsubstituted or has 1–2 substitutents each independently selected from =O, —OH, SO2 and 5- or 6-membered heterocyclic ring having 1–2 heteroatoms;

(C) phenyl which is unsubstituted or is substituted with —O—(C1–C6 alkyl) wherein the alkyl is unsubstituted or has 1–2 substituents each independently selected from the group consisting of =O and —OH, or the phenyl forms one ring of a bicyclic heterocycle containing 1–2 heteroatoms which is unsubstituted or has 1–3 substituents each independently selected from the group consisting of =O and C1–C6 alkyl which is unsubstituted or has 1–2 substituents selected from the group consisting of phenyl, =O and —OH; and (D) N(—H)—(C1–C6 alkyl) which is unsubstituted or substituted by 1–4 substituents each independently selected from the group consisting of =O, —OH and N(—H)—(C1–C6 alkyl) wherein the alkyl is unsubstituted or has 1–3 substituents each independently selected from the group consisting of phenyl, =O and —OH; or two of $R_1$, $R_2$ and Y, together with the N to which they are bound, form a 1–2 ring heterocycle with 0–1 additional heteroatoms, which is unsubstituted or substituted by 1–3 substituents independently selected from the group consisting of =O, C1–C6 alkyl wherein the alkyl is unsubstituted or has 1–2 substituents each independently selected from the group consisting of (A) =O, (B) N(—H)—(C1–C6 alkyl) which is unsubstituted or substituted by 1–2 substituents each independently selected from the group consisting of =O and —OH, (C) —O— phenyl which is unsubstituted or substituted in the phenyl with C1–C6 alkyl which is unsubstituted or substituted by 1–2 substituents each independently selected from the group consisting of =O and —OH, (D) carbocycle which is unsubstituted or substituted with C1–C6 alkyl which is unsubstituted or substituted by 1–2 substituents each independently selected from the group consisting of =O and —OH, (E) C1–C6 alkyl which is unsubstituted or substituted with 1–2 substituents each independently selected from the group consisting of (i) =O, (ii) N(—H)—(C1–C6 alkyl) which is unsubstituted or substituted by 1–2 substituents each independently selected from the group consisting of =O and —OH and (iii) a 5- or 6-membered heterocyclic ring having 1–2 heteroatoms which is unsubstituted or substituted with C1–C6 alkyl which is unsubstituted or substituted by 1–2 substituents each independently selected from the group consisting of =O and —OH, and the third of $R_1$, $R_2$ and Y is selected from the group consisting of (1)–(5) above.

In the above definition, the heteroatoms for the heterocycles are also selected from O, N and S, unless otherwise specified. Each ring of the 1–2 ringed heterocycles are 5–7 members, unless otherwise specified.

The arginine mimetic (I) in which $R_1$ and $R_2$ denote hydrogen is produced by well-known methods. Production from the precursor (II) is advantageous,

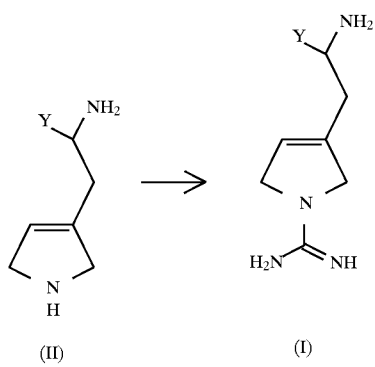

in which the primary amino group is protected preferably by reaction with phthalic acid anhydride to form the phthalimide, then the secondary amino group is amidated preferably by the methods described in Bannard et al., Can. J. Chem. 1958, 1541 and subsequently the phthalimido group is cleaved preferably by hydrazine hydrate and subsequent treatment with hydrochloric acid.

Compounds of the formula (II) in which Y denotes hydrogen can be produced by a) reducing the amide group of a compound of formula (III),

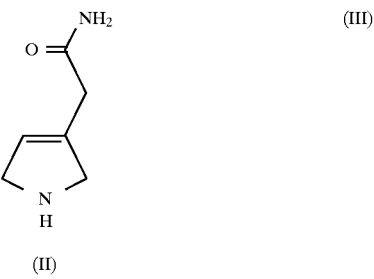

preferably with lithium aluminium hydride or lithium borohydride in the presence of trimethylchlorosilane, b) by rearranging the exocyclic double bond of a compound of the general formula

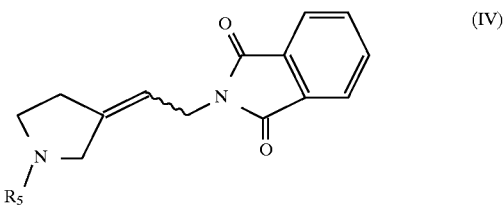

in which $R_5$ denotes a protecting group for example a benzoyl group, an alkyloxycarbonyl group or a benzyloxycarbonyl group into the isomer with an endocyclic double bond and subsequently cleaving the protecting groups. The rearrangement of the exocyclic double bond to the endocyclic double bond is carried out in the presence of lyes preferably sodium hydroxide solution as described analogously in M. I. Labouta et al., Acta Chem. Scand. Ser. B. 1982, 669–674. This is followed by the cleavage of the protecting groups $R_5$ and of the phthalimido group, or c) using the process as shown in scheme 1

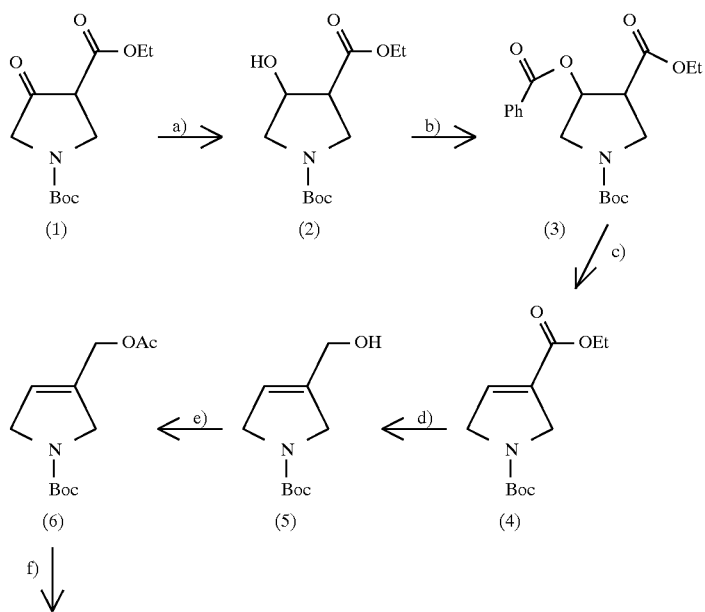

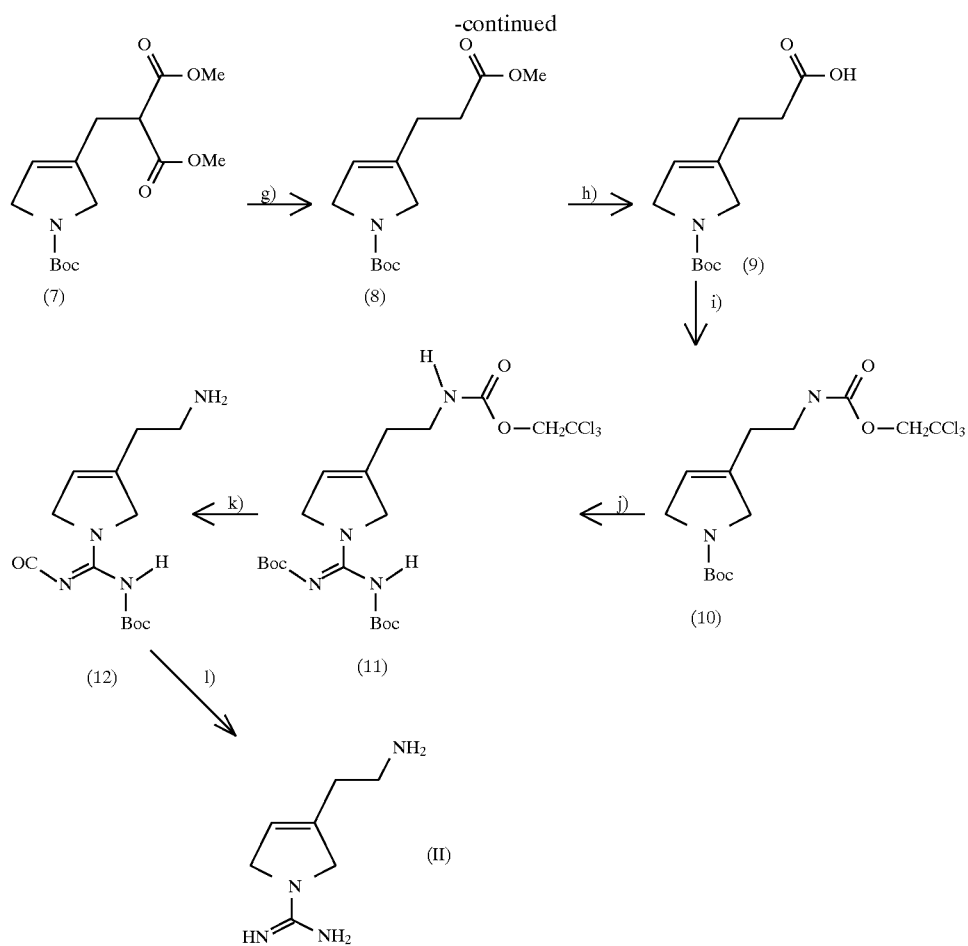

Reaction condition index to Scheme 1
a) NaBH3CN/MeOH/RT;
b) PhCOCl/Py/DMAP/RT;
c) DBU/toluene/RT/16 h;
d) DIBAL-H/THF/−78° C.;
e) Ac2O/Py/DMAP/0° C.;
f) Di-methyl-malonate/Pd(PPh3)4/TIE/20 h reflux;
g) DMF/NaCl/H2O/150° C./30 min
h) LiOH/MeOH/H2O/1N HCl
i) Diphenyl-phosphoryl-azide/THF/NEt3/80° C., 12 h; Cl3CCH2OH/THF/CuCl/2 h reflux
j) 4N HCl/16 h; (23) (scheme 2)/EtN(i-Pr)2
k) Zn/AcOH/RT
l) 4N HCl in dioxane Compounds of the general formula (II) in which Y denotes a carboxyl group can be produced according to the processes outlined in schemes 2 or 3.

SCHEME 2

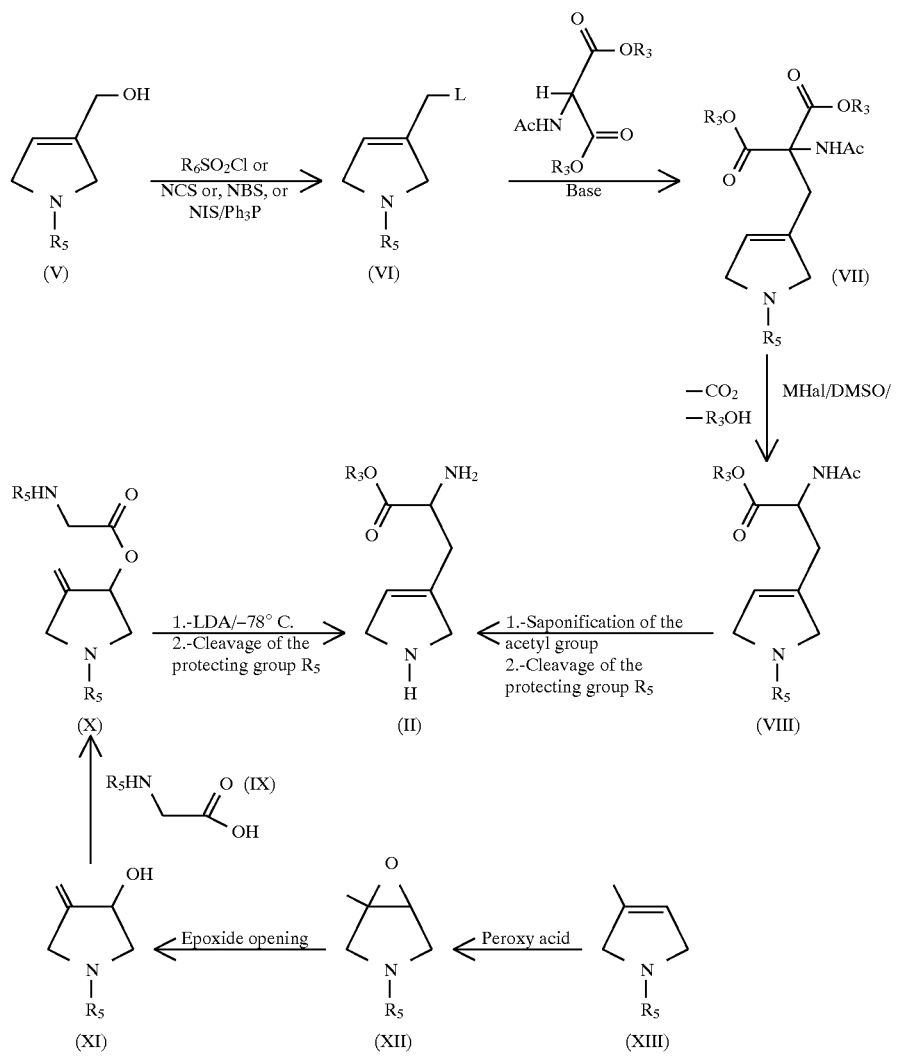

The compound (III) is produced from compounds of the general formula (XIV)

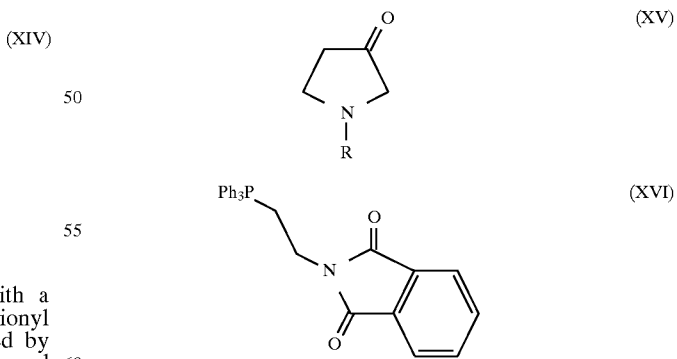

wherein $R_5$ has the above-mentioned meanings with a reagent that activates the carboxyl group for example thionyl chloride or chloroformic acid isobutyl ester followed by ammonia. Subsequently the protecting group $R_5$ is cleaved preferably with hydrochloric acid in dioxane or with trifluoroacetic acid or with hydrogen bromide in glacial acetic acid. Compounds of the general formula (XIV) are known for example from M. I. Labouta et al., Acta Chem. Scand. Ser. B, 1982, 669–674 or can be produced by the processes described in this publication.

The compounds of the general formula (IV) are produced by reacting compounds of the general formula (XV) with the compound (XVI) according to a Wittig reaction wherein R denotes for a protecting group. This Wittig reaction and the reagent (XVI) are described in Ch. Sellier et al., Liebigs Ann. Chem. 1992, 317–324. The compounds (XV) are described in A. G. Schultz, Tetrahedron 1980, 1757–1761.

Comments on scheme 2:

$R_3$ and $R_5$ have the above-mentioned meanings;

$R_6$ denotes an alkyl or aryl residue such as a methyl, ethyl, trifluoromethyl, phenyl, tosyl or 4-nitro-phenyl residue, preferably a methyl or tosyl residue;

L denotes a sulfonic acid residue such as a methanesulfonic acid, trifluoromethanesulfonic acid or p-toluenesulfinic acid residue, or a halogen such as chlorine, bromine, iodine or actate;

MHal denotes a metal halogenide such as NaCl, NaBr, KI, $MgCl_2$ or $MgBr_2$;

compounds of formula (V) are described in Timothy L. et al., J. Org. Chem. 48, 1129–1131 (1983);

Conversion of an alcohol of formula (V) into a sulfonic or acetic acid ester of formula (VI) is achieved by standard methods of organic chemistry;

The conversion of an alcohol of formula (V) into a halogenide of formula (VI) by means of N-chlorosuccinimide, N-bromosuccinimide or N-iodosuccinimide (NCS, NBS, NIS) in the presence of triphenylphosphine (Ph3P) is carried out analogously to corresponding literature methods (e.g. Rozwadowska M. D., Tetrahedron Asym., 4, 1619–1624 (1993));

A compound of formula (X) is converted into a compound of formula (II) by means of Claisen rearrangement analogously to methods which are described in Kazmaier U. et al., Tetrahedron 52, 941–954 (1996);

The epoxide opening of an epoxide of formula (XII) to form an allyl alcohol of formula (XI) is carried out under conditions which are described in Joshi V. S. et al., Tetrahedron, 24, 58'7–5830 (1968);

Compounds of formula (XIII) are described in Grubbs H. et al., J. Am. Chem. Soc., 114, 7324–7325 (1992);

The decarboxylation of malonic esters by means of metal halogenides in dimethylsulfoxide and at a high temperature is described in Krapcho A. P. et al., Tetrahedron Lett. 957 (1973).

SCHEME 3

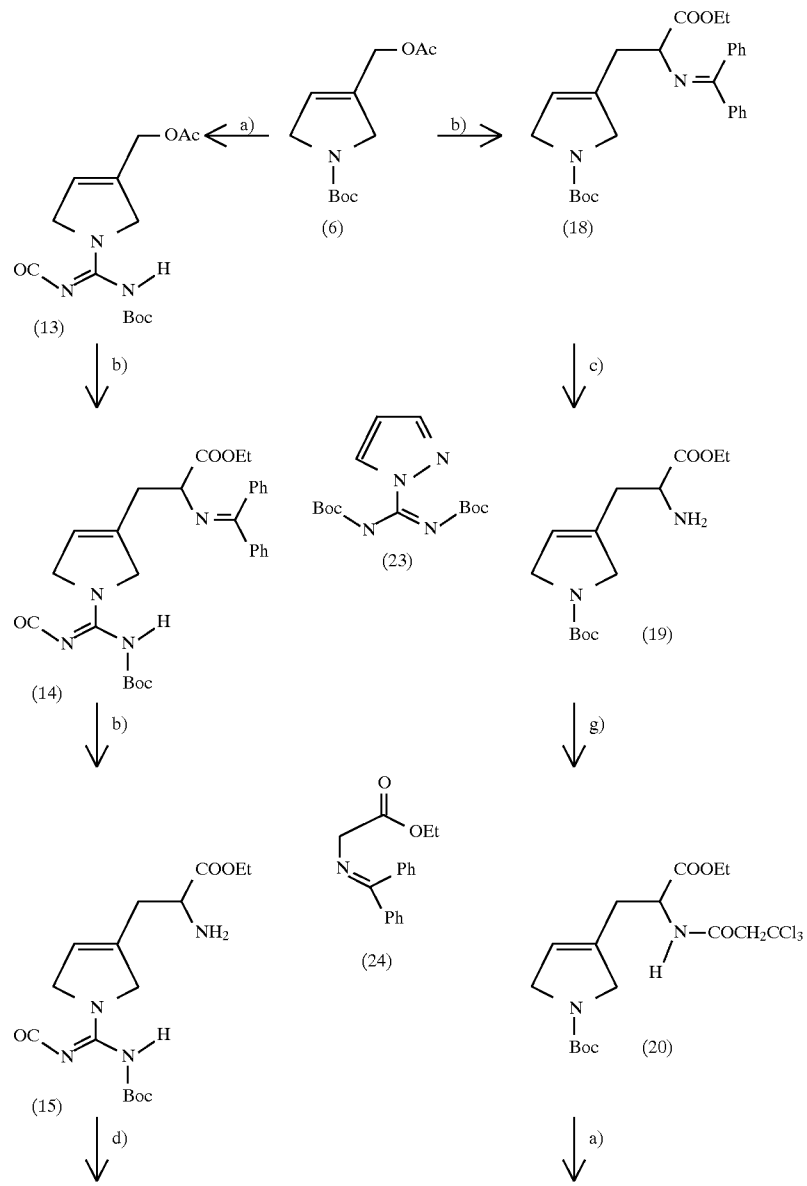

-continued
SCHEME 3

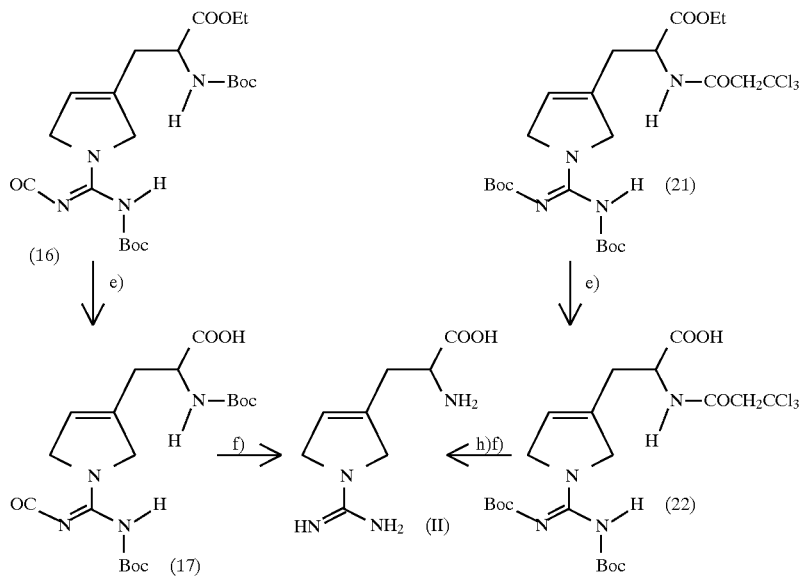

Reaction condition index to Scheme 3
a) 4N HCl/16 h; (23)/EtN(i-Pr)2
b) (24)/HMDS/n-BuLi/−78° C.
c) 1N HCl F/RT/30 min
d) Boc2O/EtN(i-Pr)2/acetonitrile/16 h
e) LiOH/THF-MeOH-H2O
f) 4N HCl in dioxane
g) Cl3CCH2OCOCl/DMAP/Py/RT/12 h
h) Zn/AcOH/RT Compounds of formula (II) as denoted in schemes 1 and 3, i.e., having the general formula

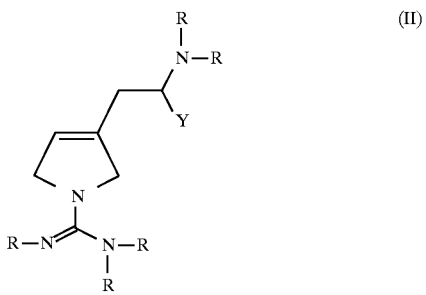

wherein each R is independently hydrogen or a protecting group and Y is hydrogen or COOH, are useful as starting materials for compounds of formula (I), and are also subject matter of the present invention. A protecting group is understood as a group that is easily attached and easily removed under conditions that will not harm other functional groups in the compound, and while it is present it is resistant to certain reagents that would otherwise attack the N it protects. It is well known to a worker of ordinary skill in the art to choose a suitable protecting group for an amino, based on the reagent which is to be employed in synthesizing a particular compound of formula (I). Suitable protecting groups for amino can be found, for example, in Morrison and Boyd, *Organic Chemistry* (Sixth Edition), Prentice Hall 1992, and Solomons, *Organic Chemistry* (Second Edition), John Wiley & Sons, Inc. 1980, which references are hereby incorporated by reference.

Some of the compounds of the general formula (I) have one or several asymmetric centers. Hence optically active forms are also a subject matter of the invention as well as tautomers.

The invention also concerns all salts of compounds of the general formula (I). Salts are primarily the acid addition salts. Physiologically acceptable salts come mainly into consideration for pharmaceutical purposes. Examples of salts of the compound of formula (I) which can be used physiologically are salts with physiologically tolerated mineral acids such as hydrochloric acid, sulfuric acid, sulfurous acid or phosphoric acid or with organic acids such as methane-sulfonic acid, p-toluenesulfonic acid, acetic acid, trifluoroacetic acid, citric acid, fumaric acid, maleic acid, tartaric acid, succinic acid or salicylic acid.

For the production of pharmaceutical agents the substances of the general formula (I) and their salts are admixed with suitable pharmaceutical carrier substances, aromatics, flavorings and dyes and are for example formed as tablets or dragees or are suspended or dissolved in water or oil for example in olive oil with addition of appropriate auxiliary substances.

The substances of the general formula (I) and their salts can be administered enterally or parenterally in a liquid or solid form. Water is preferably used as the injection medium which contains the usual additives in injection solutions such as stabilizing agents, solubilizers or buffers. Such additives are for example tartrate and citrate buffer, complexing agents (such as ethylenediamine tetraacetic acid and non-toxic salts thereof) and high molecular polymers such as liquid polyethylene oxide to regulate viscosity. Solid carriers are e.g. starch, lactose, mannitol, methylcellulose, talcum, highly-dispersed silicic acids, high molecular fatty acids (such as stearic acid) animal and vegetable fats and solid high molecular polymers (such as polyethylene glycols). Preparations which are suitable for oral administration can optionally contain flavorings and sweeteners.

The compounds of formula I are useful for treatment of diseases which are due to thromboembolic events such as stroke, myocardial infarction or arterial occlusive diseases, as well as osteoporosis, inflammations or tumour diseases. For treatment of these diseases, the compounds are usually administered in amounts of 10–1500 mg per day with regard to 75 kg body weight. It is preferred to administer 1–2 tablets with a content of active substance of 5–500 mg 2–3 times per day. The tablets can also be retarded in which case only 1–2 tablets with 20–700 mg active substance have to be administered once per day. The active substance can also be applied by injection 1–8 times per day or by continuous infusion in which case 50–2000 mg per day are usually adequate.

BRIEF DESCRIPTION OF THE FIGURES

FIG. 1: Spatial structure of Adc from D-Pla-D-Phe-L-Choi-Adc (thick rods) in the enzyme trypsin (thin rods) from the X-ray structure of example 2. The spatial structure of the inhibitor DFPR in human thrombin is superimposed over this (inhibitor: thin rods with spheres, thrombin: thin lines). The sphere represents a water molecule.

DETAILED DESCRIPTION AND PREFERRED EMBODIMENTS

The following abbreviations are used in the examples:
Ac=acetyl
Ada=(1-amidino-2,5-dihydro-1H-pyrrol-3-yl)-alanine
Adc [3-(2-aminoethyl)-2,5-dihydropyrrol-1-yl]-carbamidine
Asp=aspartic acid
Bn=benzyl
Boc=tert.butyloxycarbonyl
Bu=butyl
Cbz=benzyloxycarbonyl
Cha=cyclohexylalanine
Choi=2-carboxy-6-hydroxy-octahydroindole
DBU=1,8-diazabicyclo[5.4.0]undec-7-ene
DIBAL-H=di-isobyle aluminum hydride
DMAP=4-Dimethylaminopyridine
DMF=dimethylformamide
eq=equivalent
Et=ethyl
Fmoc=9-Fluorenylmethoxycarbonyl
Gly=glycine
HMDS=hexamethyldisilazane
i-Pr=iso-propyl
Me=methyl
NMM=N-methylmorpholine
norLeu(cyclo)-Gly=3-amino-2-oxo-hexahydro-1-azepine-acetic acid
Pcs=4-piperidine carboxylic acid
Ph=phenyl
Phe=phenylalanine
Pip=pipecolic acid
Pla=phenyllactic acid
Pmc=2,2,5,7,8-pentamethylchroman-6-sulfonyl
Pro=proline
py=pyridine
Ser=serine
t-Bu=tert.-Butyl
TBTU=2-(1H-benzotriazol-1-yl)-1.1.3.3-tetramthyluronium tetrafluorborate
TCP=Tritylchloride-polystyrene
THF=tetrahydrofuran
Troc=2.2.2-Trichlorine-ethoxycarbonyl
Tyr=tyrosine
Trp=tryptophane
$t_R$=retention time
Val=valine The C,N,O-backbone of Ada and Adc are the backbone structures which substitute the arginine or arginine mimetica structure in biological active substances of the invention, wherein OH-function of the carboxylic acid group of Ada may be replaced by another backbone atom, e.g. C, N or S.

Apart from the compounds mentioned in the examples and compounds derived by combining all meanings of the substituents stated in the claims the following are preferred within the sense of the present invention:

1. N-Me-D-Phe-Cha-Adc
2. HOOCCH2-D-Phe-Pro-Adc
3. HOOCCH2-D-Cha-Pip-Adc
4. 1-Carboxy-perhydroisoquinolinyl-Pro-Adc
5. 1-Carboxy-perhydroisoquinolinyl-N-cyclopentyl-Gly-Adc
6. EtSO2-D-Phe-Pro-Adc
7. EtSO2-D-Phe-N-cyclopentyl-Gly-Adc
8. N-(BnSO2-norLeu(cyclo)-Gly-Adc 9.3-({3-[2-(1-Amidino-2,5-dihydro-1H-pyrrol-3-yl)-ethyl]-2,4-dioxo-1,2,3,4-tetrahydo-quinazolin-6-carbonyl}-amino)-propionic acid
10. (4-{3-[2-(1-amidino-2,5-dihydro-1H-pyrrol-3-yl)-ethyl]-2-oxo-oxazolidin-5oxy}-phenyl)-acetic acid
11. 3-({1-[2-(1-Amidino-2,5-dihydro-1H-pyrrol-3-yl)-ethylcarbamoyl]-piperidin-3-carbonyl}-amino)-3-pyridin-2-yl-propionic acid
12. (4-{[2-(1-Amidino-2,5-dihydro-1H-pyrrol-3-yl)-ethylamino]-acetyl}-3- methoxycarbonyl-methyl-piperazin-1-yl)-acetic acid
13. [4-({[2-(1-Amidino-2,5-dihydro-1H-pyrrol-3-yl)-ethyl]-methylamino}-acetyl)-phenoxy]-acetic acid
14. {7-[2-(1-Amidino-2,5-dihydro-1H-pyrrol-3-yl)-ethylcarbamoyl]-3-oxo-4-phenethyl-2,3,4,5-tetrahydro-1H-benzo[e][1,4]diazepin-2-yl}-acetic acid
15. 3-(4-{3-[2-(1-Amidino-2,5-dihydro-1H-pyrrol-3-yl)-ethyl]-2-oxo-imidazolidin-1-yl)}-phenyl) propionic acid
16. 4-{3-[2-(1-Amidino-2,5-dihydro-1H-pyrrol-3-yl)-ethyl]-2-oxo-imidazolidin-1-yl}-cyclohexane carboxylic acid
17. [5-(4-{[2-(1-Amidino-2,5-dihydro-1H-pyrrol-3-yl)-ethylamino]-methyl}-phenoxymethyl)-2-oxo-pyrrolidin-3-yl]-acetic acid
18. [5-({4-[2-(1-Amidino-2,5-dihydro-1H-pyrrol-3-yl)-ethylamino]-piperidin-1yl}-acetyl)-2-carboxymethoxy-phenoxy]-acetic acid
19. (4-{[2-(1-Amidino-2,5-dihydro-1H-pyrrol-3-yl)-ethyl]-methyl-amino}-[1,4']bipiperidinyl-1'-yl)-acetic acid
20. 3-{3-[2-(1-Amidino-2,5-dihydro-1H-pyrrol-3-yl)-ethylcarbamoyl]-propionylamino }-butyric acid
21. 3-{3-[2-(1-Amidino-2,5-dihydro-1H-pyrrol-3-yl)-ethylcarbamoyl]-propionylamino}-3-phenyl-propionic acid
22. 3-{3-[2-(1-Amidino-2,5-dihydro-1H-pyrrol-3-yl)-ethylcarbamoyl]-propionylamino}-3-pyridin-2-yl-propionic acid
23. 3-{3-[2-(1-Amidino-2,5-dihydro-1H-pyrrol-3-yl)-ethylcarbamoyl]-propionylamino}-pent-4-ynone carboxylic acid
24. 3-(2-{3-[2-(1-Aridino-2,5-dihydro-1H-pyrrol-3-yl)-ethyl]-ureido}-acetylamino)-N-(carboxy-phenyl-methyl)-succinic acid
25. 3-(2-{3-[2-(1-Amidino-2,5-dihydro-1H-pyrrol-3-yl)-ethyl]-2-oxo-tetrahydro-pyrimidin-1-yl}-acetylamino)-propionic acid
26. {4-[2-(1-Amidino-2,5-dihydro-1H-pyrrol-3-yl)-ethylamino]-cyclohexyl}-acetic acid
27. 3-(Butane-1-sulfonyl)-2-(4-{[2-(1-amidino-2,5-dihydro-1H-pyrrol-3-yl)-ethylamino]-methyl}-benzyl)-propionic acid
28. 2-{2-[2-Amino-3-(1-amidino-2,5-dihydro-1H-pyrrol-3-yl)-propionylamino]-acetylamino}-succinic acid
29. 1-{3-[2-(1-Amidino-2,5-dihydro-1H-pyrrol-3-yl)-ethyl]-2-oxo-oxazolidin-5-ylmethyl}-piperidin-4-carboxylic acid
30. Ada-Gly-Asp-Ser 31. Ada-Gly-Asp-Ser-NH2
32. Ada-Gly-Asp-Phe
33. Ada-Gly-Asp-Phe-NH2
34. Ada-Gly-Asp-Tyr
35. Ada-Gly-Asp-Tyr-NH2
36. Ada-Gly-Asp-Trp
37. Ada-Gly-Asp-Trp-NH2
38. Ada-Gly-Asp-Val
39. Ada-Gly-Asp-Val-NH2
40. Pla-Phe-Choi-Adc

EXAMPLE 1

D-Pla-D-Phe-L-Choi-Adc

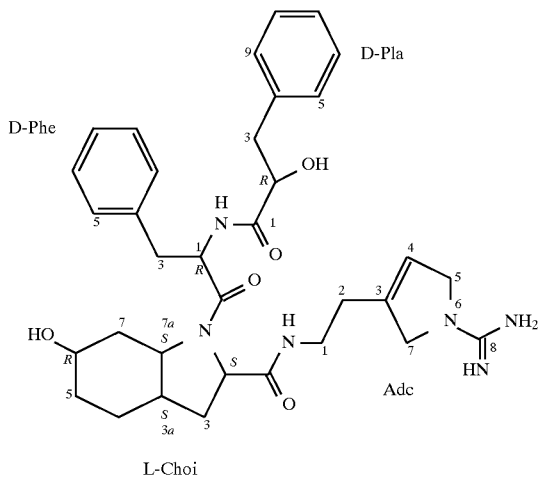

Production of the biomass

Three 20 l glass cylinders with a pH regulator were filled with sterile filtered nutrient medium, each was inoculated with 50 ml preculture of Oscillatoria agardhii from the collection of algae cultures of the Institute of Plant Physiology of the University of Göttingen (strain number B3.82) and incubated for ca. 14 days at a constant pH of 8.5, a temperature of 20° C. and an average irradiation of 30 Wm-2 under continuous gassing with sterile-filtered room air.
Nutrient medium 3.6 mg CaCl2×2 H2O, 20.3 mg Ca(NO3)2×4 H2O, 2.7 mg KCl, 1.5 mg K2HPO4, 76.0 mg MgSO4×7 H2O, 84.0 mg NaHCO3, 1 ml trace element solution, 1000 ml deionized water.

Trace element solution: 875 mg Na4EDTA, 9.7 mg Co(NO3)2×6 H2O, 284 mg FeCl2×6 H2O, 72.2 mg MnCl2×4 H2O, 25.2 mg Na2MoO4×2 H2O, 43.7 mg ZnSO4×7 H2O, 1000 ml deionized water. (K. Zielinski, Dissertation, Univ. Freiburg, 1988, p.23)
Processing of the 3×20 l cultures At the time of harvesting the three 20 l cultures were combined and the cells and nutrient solution were separated by gentle centrifugation (5000 g, 10 min). The biomass was frozen at −20° C. and subsequently lyophilized.

The lyophilisate (ca. 30 g) was extracted once with 1000 ml and twice with 500 ml methanol and the combined methanol phases were evaporated to dryness. The methanol extract (ca. 7 g) was taken up in 500 ml water and shaken out three times with 500 ml butanol each time. The butanol phases were combined and concentrated to dryness at 40° C. on a rotary evaporator.

The butanol extracts were combined (ca. 5 g), taken up in 150 ml methanol and absorbed onto ca. 25 g LiChroprep-CN phase (25–40 μm) and chromatographed over a LiChroprep-CN column (column: 52×356 mm; mobile phase gradient: water/acetonitrile/trifluoroacetic acid from (100:0:0:1) to (50:50:0.1), total elution volume: 5l).

The fractions containing D-Pla-D-Phe-L-Choi-Adc which were identified with the aid of TLC or the thrombin time prolongation assay were pooled and evaporated to dryness at 40° C. on a rotary evaporator.

The concentrate (ca. 1g) was dissolved in 100 ml methanol, absorbed to ca. 5 g silica gel LiChroprep Si60 (15–25 μm) and chromatographed over a silica gel column (26×360 mm) with 1500 ml chloroform/methanol/glacial acetic acid/water (65:25:3:4) as the mobile solvent.

The pooled and concentrated fractions containing D-Pla-D-Phe-L-Choi-Adc (ca. 200 mg) were taken up in 3 ml methanol for the further purification and further separated by high pressure liquid chromatography on Nucleosil-100 RP18 (10 μm, column: 20×250 mm) with water/acetonitrile/trifluoroacetic acid (70:30:0.1) as the mobile solvent.

The concentrated fraction containing D-Pla-D-Phe-L-Choi-Adc (20 mg) was taken up in 1 ml methanol and subjected to a further high pressure liquid chromatography (column: Nucleosil-100 RP 18, 10 μm, 20×250 mm; mobile solvent: 50 mM phosphate buffer pH 7.8/acetonitrile (70:30)). A fraction was obtained which only contained D-Pla-D-Phe-L-Choi-Adc. This was concentrated to ca. 5 ml aqueous solution.

In order to remove the buffer the aqueous concentrate was applied to a Nucleosil-100 RP 18 column (15×100 mm), whereby D-Pla-D-Phe-L-Choi-Adc was bound to the stationary phase. After washing with 100 ml water, the D-Pla-D-Phe-L-Choi-Adc was eluted with 200 ml water/methanol (10:90). The methanolic eluate was evaporated to dryness at 40° C. on a rotary evaporator. ca. 3 mg pure D-Pla-D-Phe-L-Choi-Adc was obtained as a colourless phosphate salt.

Analytical data for D-Pla-D-Phe-L-Choi-Adc a) Mass spectrometry

The LSIMS spectrum of D-Pla-D-Phe-L-Choi-Adc yielded a pseudomolecule ion at MH+617 Da. High resolution measurements in the positive LSIMS mode resulted in MH+617.345 Da which enabled C34H44N6O5 to be derived as the elemental composition of the neutral compound. The MS/MS spectrum of the molecular ion MH+ produced a series of daughter ions which confirmed the chemical structure derived for D-Pla-D-Phe-L-Choi-Adc.

Experimental conditions

The compound was measured at a resolution of ca. 5000 in the LSIMS mode against PEG as the reference substance in the peak match mode.

Experimental data

LSIMS selected peaks (M/Z:rel.int.) 136:92; 154:100; 176:9; 193:6; 239:6; 289:14; 307:19; 331:3; 358:34; 381:2; 399:6; 469:2; 525:3; 593:7; 617:86; 647:8; 667:3; 713:6.

MS/MS of MH+ selected peaks (M/Z:rel. int.) 94:10; 120:64; 140:39; 153:3; 181:9; 209:16; 250:2; 268:7; 305:1; 320:13; 349:1; 377:3; 453:2; 469:16; 540:3; 565:5

Assignment of the fragments (daughter ions)

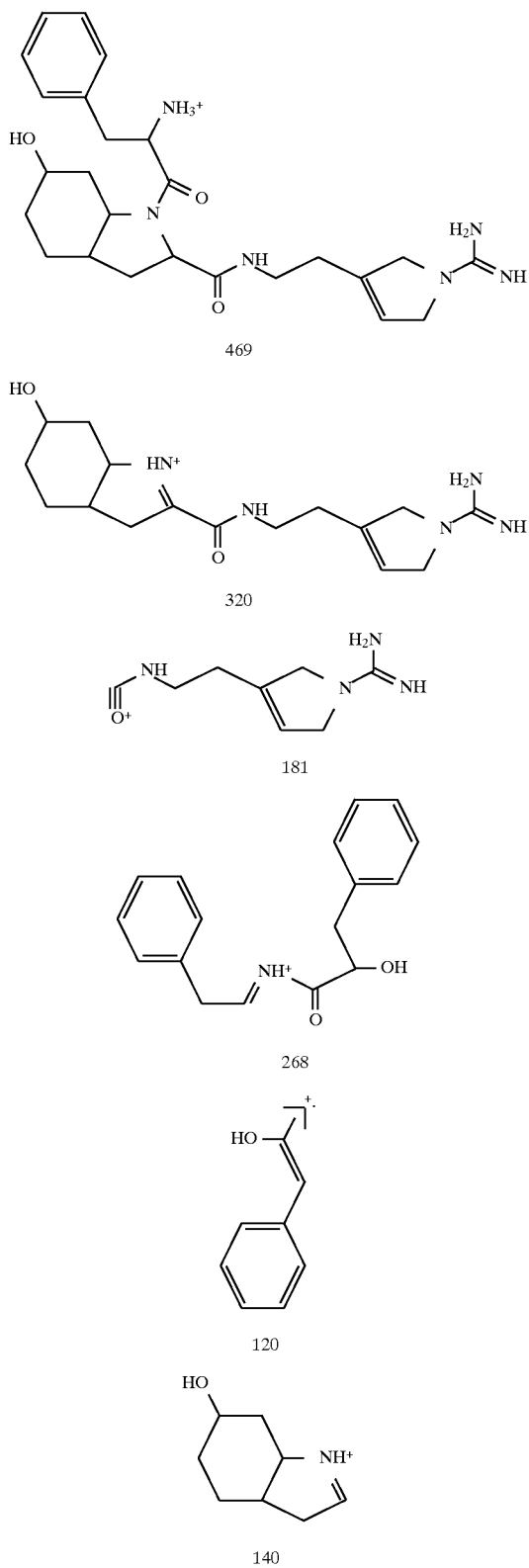

(b) Gas chromatographic analysis of the acid total hydrolysate of D-Pla-D-Phe-L-Choi-Adc The molecular components D-Pla and D-Phe could be detected in the acid total hydrolysate of D-Pla-D-Phe-L-Choi-Adc by gas chromatographic analysis on a chiral phase. Furthermore a peak was identified in the gas chromatogram by means of GC-MS coupling which could be assigned in the EI mass spectrum to the molecular component Choi on the basis of the two typical masses of 419 Da (the molecular ion (M+) of N,O-di-trifluoroacetyl-Choi-n-propyl ester) and 332 Da (the fragment [M—C(O)OC3H]+).
Experimental conditions The sample was hydrolyzed for 24 h with 6N hydrochloric acid and derivatized after blowing off the hydrochloric acid.

0.5 ml 4N hydrochloric acid in n-propanol was added to the dry hydrolysate for the detection of D-Phe and Choi and the reaction mixture was heated for 30 minutes to 110° C. The excess reagent was completely blown off. The subsequent acylation was carried out for 10 minutes at 150° C. with trifluoroacetic acid anhydride. The reagent was again completely blown off and the sample was taken up in solvent.

For the detection of D-Pla 0.5 ml 4N hydrochloric acid in methanol was added to the dry hydrolysate and the reaction mixture was heated for 10 minutes to 110° C. The excess reagent was completely blown off. The subsequent aminolysis was carried out at room temperature with n-propylamine. Afterwards it was silylated for 20 minutes at 70° C. with hexamethyldisilazane.

The derivatized products of hydrolysis were analysed by capillary gas chromatography on a chiral phase. A 20 m capillary with an inside diameter of 0.28 mm and a film thickness of 0.25 μm was used which is covered with Chirasil Val. A flame-ionization detector was used for the detection. The peaks were assigned in the case of D-Phe and D-Pla by comparing the retention with those of reference substances. In the case of Choi a sector field mass spectrometer was used for the detection.

(c) NMR spectroscopy

The structure of the compound of example 1 was elucidated and confirmed by NMR spectroscopy (2D NMR, HMBC, HMQC, COSY (DQF-H,H-COSY, E.COSY), TOCSY, ROESY).

EXAMPLE 2

The compound of example 1 cocrystallizes with the bovine serine protease trypsin. It was possible to derive the connectivity of the inhibitor in the complex with bovine trypsin from the high resolution crystal structure of the serine protease inhibitor D-Pla-D-Phe-L-Choi-Adc. Comparison with an arginine-containing inhibitor showed that D-Pla-D-Phe-L-Choi-Adc contains an arginine mimetic.

The inhibitor D-Pla-D-Phe-L-Choi-Adc resembles the known thrombin inhibitor (D)-Phe-Pro-Arg (DFPR) along the main chain. There are differences at the N-terminus (an additional residue), at the proline analogue (a condensed ring with a hydroxy group) and at the C-terminus (no carboxylate and a guanidino group partially integrated into a five-membered ring).

A comparison between the X-ray structure of D-Pla-D-Phe-L-Choi-Adc with trypsin and that of the trombin-DFPR complex (Bode, W., Mayr, I., Baumann, U., Huber, R., Stone, S., & Hofsteenge, J. (1989). EMBO Journal 8, 3467–3475) clearly showed this similarity. If both X-ray structures are superimposed, the DFPR inhibitor lies within the electron density of D-Pla-D-Phe-L-Choi-Adc. Deviations only occur with respect to the differences in the side chain described above.

The Fo-Fc electron densities phased independently of the stated inhibitor structure confirmed the chemical structure of the molecular building block Adc. The five-membered ring is obvious. The spatial geometry of the electron density corresponds to a double bond in an equivalent position to the C of arginine. The planarity of the density is also consistent with a nitrogen atom in the N equivalent position. From this the guanidino group is deduced.

The refinement of the X-ray structure of the inhibitor D-Pla-D-Phe-L-Choi-Adc with the protein structure—at first with the appropriate geometric restraints, subsequently without any restraints—showed that the molecular building block Adc of D-Pla-D-Phe-L-Choi-Adc binds as an arginine analogue (FIG. 1). The additional ring atoms replace a water molecule. The other specific hydrogen bridges as well as the spatial position of the corresponding atoms remain almost identical.

DESCRIPTION OF THE METHODS OF X-RAY STRUCTURAL ANALYSIS

Crystallization

Bovine β-trypsin (SIGMA) was repurified (D. D. Schroeder, E. Shaw (1968) J. Biol. Chem. 243, 2943–2949) and lyophilized. For crystallization preparations 3.5 mg of the lyophilisate (70 % w/w beta trypsin, 20% benzamidine, 10 % CaCl2) was dissolved in 30 μl distilled H2O and mixed 1:1 with the precipitating solution (1.6M ammonium sulfate, 100 mM imidazole/H2SO4, pH 6, 0.02% sodium azide). Crystals were produced by vapour diffusion (6 μl drops protein solution/4 ml precipitation solution). Benzamidine was replaced by D-Pla-D-Phe-L-Choi-Adc in the crystal by successive soaking: 1) twice for 2 hours in a pure harvest solution (2.5M ammonium sulfate, TRIS/HCl pH 8, 10 mM CaCl2) in order to remove benzamidine and 2) overnight in inhibitor solution (1.76 mg D-Pla-D-Phe-L-Choi-Adc dissolved in 176 μl harvest solution).

Data collection, evaluation

The crystal was oriented with a 4-circle goniometer from Siemens. The X-ray source was a copper rotating anode Rigaku Rotaflex-generator (45 kV, 120 mA) equipped with a curved graphite monochromator. The diffracted reflexes were measured with a Siemens X1000 area counter. A total of 2464 recordings (width 0.1 degree) of four orientations were made corresponding to a theoretical completeness of 99% for a resolution of 1.6 A (estimated with the program ASTRO (Siemens Industrial Automation, Inc., Madison, Wis., USA)). Automated indexing and data evaluation were carried out using SADIE and SAINT (Siemens Industrial Automation, Inc., Madison, Wis.) (see Table 1).

Table 1: Crystallographic data and refinement statistics

Recording turning range: 0.1 degree
crystal detected removal: 11.65 cm recording time:90 sec.
total number of recordings: 541+541+541+841=2464
cell dimensions: 63.31A, 63.57A, 69.06A, 90 deg, 90 deg, 90 deg.
spatial group: P2(1)2(1)2(1)
total reflexes: 65572
independent reflexes: 40648
positive reflexes: 34497
positive reflexes after 2 sigma selection: 28962
Total R-merge (5–1.5A): 4.2%
Completeness after resolution

| Resolution: | % in resolution shell | Total |
|---|---|---|
| 2.90, 6.00 | 85.3264 | 85.3264 |
| 2.35, 2.90 | 95.2330 | 90.2261 |
| 2.06, 2.35 | 91.3768 | 90.6049 |
| 1.88, 2.06 | 83.5322 | 88.8642 |
| 1.75, 1.88 | 68.6958 | 84.8784 |
| 1.65, 1.75 | 50.7991 | 79.2804 |
| 1.57, 1.65 | 28.7895 | 72.1611 |
| 1.50, 1.57, | 14.5349 | 65.0376 |

Model refinement
 (p=protein,s=solvent,i=inhibitor; r=rigid body refinement, c=Powell conjugate gradients refinement, t=B-factor refinement; b=bonds, a=angles)

| Cycle | ATOMS (p,s,i) | % R-factor (r,c,t) | RMS from ideality (b,a) |
|---|---|---|---|
| 1 | 1630, 23, 0 | 28.7, 27.2, 23.4 | 0.007, 1.97 |
| 2 | 1630, 23, 0 | —, 22.8, 22.5 | 0.006, 1.72 |
| 3 | 1630, 23, 34 | —, 21.7, 21.5 | 0.007, 1.74 |
| 4 | 1630, 23, 45 | —, 21.5, 21.4 | 0.006, 1.80 |

Electron density calculation, interpretation

The first electron density was phased with the 1.5 A resolved P2(1)2(1)2(1) X-ray structure of trypsin (H. D. Bartunik, J. Summers, H. H. Bartsch, J. Mol. Bio. 210, 813, 1989) from the Brookhaven databank (1TLD, Abola, E. E. Bernstein, F. C., Bryant, S. H. Koetzle, T. F. & Weng, J. (1987) in Crystallographic databases—Information Content, Software Systems, Scientific Applications, Allen, F. H., Berghoff & G., Sievers, R., eds., Data Commission of the International Commission of the International Union of Crystllography (Bonn/Cambridge/Chester, 1987), 107–132) after structural and B factor refinement using XPLOR (Molecular Simulations Incorporated MSI AG, Basel Switzerland). This density clearly showed the general orientation of the inhibitor. Additional refinement cycles improved the densities and thus enabled the determination of the connectivities of the basic group in D-Pla-D-Phe-L-Choi-Adc. It was also possible to likewise determine all other positions of the inhibitor except the first phenyl ring of oscillarin which probably binds in a disordered manner.

EXAMPLE 3

HOOC-CH2-D-Cha-(N-cyclopentyl)-Gly-Adc

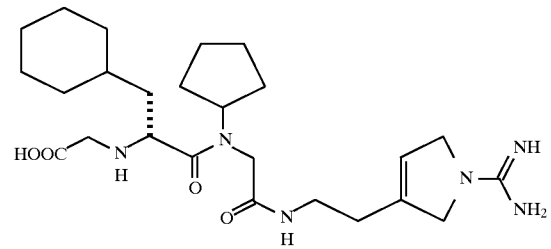

(a) 4-Oxo-pyrrolidine-1,3-dicarboxylic acid 1-tert. butylester 3-ethylester (J. Cooper et al. J. Chem.Soc.Perkin Trans. 1, 1993, 1313–1318)

To a refluxing suspension of 1.58 g (66 mmol) sodium hydride in 100 ml THF was added dropwise a solution of 12.79 g (60 mmol) N-tert-butyloxycarbonyl-glycine ethyl ester and 7.15 g (66 mmol) ethyl acrylate in 100 ml THF. After the addition was complete the mixture was heated to reflux for additional 2 h. The clear solution was cooled to room temperature, poured on 100 ml ether/100 ml water and acidified under vigorous stirring with 1N hydrochloric acid against methyl orange. The layers were separated and the aqueous layer was extracted three times with ether. The combined organic layers were washed with sat. sodium bicarbonate and brine, dried over MgSO4 and evaporated. Short-path distillation of the residue gave 10.92 g (71%) 4-oxo-pyrrolidine-1,3-dicarboxylic acid 1-tert. butylester 3-ethylester as a colorless oil, b.p. 119°–122° C. (0.2 mbar), which solidified on prolonged standing in the freezer.

GC/MS (BP 5890 II/HP 5972; column: HP 5,30 m×25 mm×0.25 (m film thickness, carrier gas: helium; temperature gradient: 50° C., 3 min; then with 20° C./min to 250° C.)

$t_R$=9.68 min m/z [%]=185 (2), 130 (10), 112 (18), 85 (6), 57 (100).

b) 4-Hydroxy-pyrrolidine-1,3-dicarboxylic acid 1-tert.-butylester 3-ethylester

To a solution of 5.15 g (20 mmol) 4-oxo-pyrrolidine-1,3-dicarboxylic acid 1-tert. butylester 3-ethylester in 30 ml methanol was added 1.88 g (30 mmol) sodium cyanoborohydride and a small amount of methylorange. With stirring the pH was adjusted to 3 by dropwise addition of 1N hydrochloric acid (color change from yellow to orange). After no more acid was consumed the mixture was stirred for one hour. The solvent was evaporated in vacuo and the residue was partitioned between ethyl acetate and water. The organic layer was washed twice with water, then with brine, dried over magnesium sulfate and evaporated. The residual yellow oil was used in the next step without any further purification.

GC/MS (HP 5890 II/HP 5972; column: HP 5,30 m×25 mm×0.25 (m film thickness, carrier gas: helium; temperature gradient: 50 ° C., 3 min; then with 20 ° C./min to 250 ° C.;)

$t_R$=12.44 min (no separation of diastereomers)

m/z [%]=259 (M+,0.3), 241 (0.7), 202 (5), 186 (7), 158 (10), 112 (14), 68 (31), 57 (100).

c) 4-Benzoyloxy-pyrrolidine-1,3-dicarboxylic acid 1-tert.-butylester 3-ethylester To an ice-cooled solution of the crude 4-hydroxy-pyrrolidine-1,3-dicarboxylic acid 1-tert.-butylester 3-ethylester from the reduction described above and 244 mg (2 mmol) DMAP in 40 ml pyridine were added dropwise 3.51 g (25 mmol) benzoyl chloride. After the addition was complete, the ice bath was removed and the mixture was stirred at room temperature for 2 h. The mixture was diluted with ethyl acetate an poured on ice. The organic layer was separated, washed with water, sat. CuSO4, water and brine, dried over MgSO4 and evaporated. The residual yellow oil was used in the next step without further purification.

GC/MS (BP 5890 II/HP 5972; column: HP 5,30 m×25 mm×0.25 (m film thickness, carrier gas: helium; temperature gradient: 50° C. 3 min; then with 20° C./min to 250° C.)

$t_R$=17.28 and 17.38 min (1:1-mixture of cis/trans-isomers)

m/z[%]=318 (0.1),290 (5),262 (2),241(2),185 (29),141 (10), 112 (23), 105 (53), 77 (27), 68 (100), 57 (97).

d) 2,5-Dihydro-pyrrole-1,3-dicarboxylic acid 1-tert.-butylester 3-ethyl ester

To a solution of the crude 4-benzoyloxy-pyrrolidine-1,3-dicarboxylic acid 1-tert.-butylester 3-ethylester from the benzoylation described above in 75 ml dry toluene was added 4.11 g (27 mmol) DBU. The dark, heterogeneous mixture was stirred at room temperature for 16 h. After this time no starting material was detectable by TLC and GC analysis. The mixture was filtered through a short column of silica (elution with petrolether/ethyl acetate 1:1) and evaporated. Bulb-to-bulb distillation of the residual slightly yellow oil gave 4.16 g (86%) 2,5-dihydro-pyrrole-1,3-dicarboxylic acid 1-tert.-butylester 3-ethyl ester as a colorless oil b.p. 110° C./0.2 mbar, which slowly solidified to a waxy mass on standing in the freezer.

GC/MS (HP 5890 II/HP 5972; column: HP 5,30 m×25 mm×0.25 (m film thickness, carrier gas: helium; temperature gradient: 50° C. 3 min; then with 20° C./min to 250° C.)

$t_R$=11.94 min m/z [%]=241 (M+, 1.4), 196 (0.4), 185 (11),168 (11), 140 (14), 112 (17), 68 (24), 57 (100).

$^1$H-NMR (CDCl3, 300 MHz) δ=1.27 (t, J=7.1 Hz, 3H, OCH2CH3), 1.43, 1.44 [2s, 9H, C(CH3)3]$^\#$, 4.25 (d, J=7.1 Hz, 2H, OCH2CH3), 4.15–4.27 (br. m, 4H, 2-H, 5-H), 6.66–6.71 (m, 1H, 4-H) ppm. $^\#$Double set of signals due to hindered rotation.

$^{13}$C-NMR (CDCl3, 75 MHz) δ=14.16, 14.20 (q,—CH2–CH3)*, 28.45 [q, —C(CH3)3], 51.76, 51.99, 53.62, 53.84 (4t, C-2, C-5)*, 60.69 (t, —CH2–CH3),79.84 [s, —C(CH3)3], 132.29 (s, C-3), 136.44, 136.55 (2d, C-4)*, 153.86, 154.08 (2s, —NCOO—)*, 162.75 (s, COOEt) ppm.

e) 3-Hydroxymethyl-2,5-dihydro-pyrrole-1-carboxylic acid tert.-butylester

To a solution of 5.43 g (22.5 mmol) 2,5-dihydro-pyrrole-1,3-dicarboxylic acid 1-tert.-butylester 3-ethyl ester in 50 ml THF, cooled to –78° C. was dropwise added 50 ml of a 1N DIBAL-H solution in hexane. The mixture was allowed to warm to room temperature overnight. As TLC analysis indicated complete consumption of starting material, the mixture was cooled in an ice bath and 1.90 g water were cautiously added, followed by 1.90 g 15% aqueous NaOH and 5.70 g water. The white precipitate was filtered off, washed thoroughly with ether and the combined filtrates were evaporated. Bulb-to-bulb distillation of the residual pale yellow oil gave 4.13 g (93%) 3-hydroxymethyl-2,5-dihydro-pyrrole-1-carboxylic acid tert.-butylester as a colorless oil, b.p. 130° C. (0.2 mbar).

GC/MS (HP 5890 II/HP 5972; column: HP 5,30 m×25 mm×0.25 (m film thickness, carrier gas: helium; temperature gradient: 50° C. 3 min; then with 20° C./min to 250° C.)

$t_R$=11.34 min m/z [%]=199 (M+, 1), 143 (10), 142 (13), 126 (13), 112 (12), 80 (10), 68 (45), 57 (100).

$^1$H-NMR (CDCl3, 300 MHz) δ=1.44 (s, 9H, t-Bu), 4.09 (br. m, 4H, 2-H, 4-H), 4.18 (br. s, 2H, CH2OH), 5.63 (br.d, 1H, 4-H) ppm.

$^{13}$C-NMR (CDCl3, 75 MHz) δ=28.5 [q, C(CH3)3], 52.8, 53.0, 53.2, 53.3 (4t, C-2, C-5)$^\#$, 57.7, 59.8 (2d, CH2OH), 79.5 [s, C(CH3)3], 120.0, 120.3 (2d, C-4), 139.6 (s, C-3), 154.4 (s, COOtBu) ppm. $^\#$Double set of signals due to hindered rotation f) 3-Acetoxymethyl-2,5-dihydro-pyrrole-1-carboxylic acid tert.-butylester To an ice-cooled solution of 4.13 g (20.7 mmol) 3-hydroxymethyl-2,5-dihydro-pyrrole-1-carboxylic acid tert-butylester and 244 mg (2 mmol) DMAP in 50 ml pyridine was added 3.06 g (30 mmol) acetic anhydride. The mixture was stirred for 30 min at 0° C., then for additional 60 min at room temperature. The mixture was poured on ice and extracted twice with ether. The combined organic layers were evaporated in vacuo, dissolved in ether, washed with sat. CuSO4, water and brine and dried over MgSO4. Evaporation and bulb-to-bulb distillation gave 4.82 g (97%) 3-acetoxymethyl-2,5-dihydro-pyrrole-1-carboxylic acid tert.-butylester as a colorless oil, b.p. 105° C. (0.2 mbar).

GC/MS (BP 5890 II/HP 5972; column: HP 5,30 m×25 mm×0.25 (m film thickness, carrier gas: helium; temperature gradient: 50° C. 3 min; then with 20° C./min to 250° C.)

$t_R$=11.87 min m/z [%]=241 (M+, 0.2), 226 (0.1), 185 (5), 166 (5), 125 (18), 108 (3), 81 (13), 80 (23), 57 (100).

$^1$H-NMR (CDCl3, 300 MHz) δ=1.43, 1.44 [2s, 9H, C(CH3)3]*, 2.04, 2.06 (2s, 3H, OOCCH3)*, 4.05–412 (br.m, 4H, 2-H, 5-H), 4.61 (br. d, J=5.7 Hz, 2H, CH2O), 5.66–5.73 (br. m, 1H, 4-H)ppm.

$^{13}$C-NMR (CDCl3, 75 MHz) δ=20.7 (q, OOCCH3),28.4 [q, C(CH3)3], 53.0, 53.2, 53.3 (3t, 2-C, 5-C)*,60.8 (t, CH2OAc), 79.5 [s, C(CH3)3], 123.4, 123.8 (2d, C-4)*, 134.5, 134,6 (2s, C-3), 154.1 (s, NCOO), 170.5 (s, OOCCH3) ppm.

g) 2-(1-tert.-Butoxycarbonyl-2,5-dihydro-1H-pyrrol-3-yl-methyl)-malonic acid dimethylester 5.28 g (40 mmol) dimethyl malonate were cautiously added to an ice-cooled suspension of 864 mg (36 mmol) sodium hydride in 80 ml THF. The resulting clear solution was added to a solution of 4.82 g (20 mmol) 3-acetoxymethyl-2,5-dihydro-pyrrole-1-carboxylic acid tert.-butylester and 462 mg (0.4 mmol) Pd(PPh3)4 in 40 ml THF and the mixture was heated to reflux for 20 h. The reaction mixture was cooled to room temperature, diluted with ether and quenched with sat. NH4Cl. The organic layer was washed with sat. NH4Cl and brine, dried over MgSO4 and evaporated. The residue was purified by flash chromatography (ethyl acetate/petrol ether 4:1 to 2:1) and bulb-to-bulb distilled to yield 4.86 g (77%) of 2(1-tert.-butoxycarbonyl-2,5-dihydro-1H-pyrrol-3 -yl-methyl)-malonic acid dimetylester as a colorless oil, b.p. 130° C./0.2 mbar.

GC/MS (HP 5890 II/HP 5972; column: HP 5,30 m×25 mm×0.25 (m film thickness, carrier gas: helium; temperature gradient: 50° C., 3 min; then with 20° C./min to 250° C.)

$t_R$=14.07 min m/z [%]=313 (M+, 0.1), 257 (27), 240 (5), 126 (35), 82 (59), 80 (38), 57 (100).

$^1$H-NMR (CDCl3, 300 MHz) δ=1.43, 1.44 [2s, 9H, C(CH3)3]*, 2.68 (m, 2H, 3-CH2), 3.57 [t, J=6.6 Hz, 1H, CH(COOCH3)2], 3.71, 3.72 [2s, 6H, CH(COOCH3)2], 3.97–4.10 (br. m, 4H, 2-H, 5-H), 5.44 (br. m, 1H, 4-H) ppm.

$^{13}$C-NMR (CDCl3, 75 MHz) δ=28.0, 28.1 (2t, 3-CH2-), 28.5 [q, C(CH3)3], 50.1 [d, CH(COOMe)2]52.7 (q, OCH3), 53.1, 53.3, 54.5, 54.9 (4t, C-2, C-5)*, 79.4 [s, C(CH3)3], 121.0 (d, C-4), 135.8 (s, C-3), 154.1 (s, NCOO), 169.0 (s, COOMe) ppm.

h) 3-(2-Methoxycarbonyl-ethyl)-2,5-dihydropyrrole-1-carboxylic acid tert. butyl ester To a solution of 4.52 g (14.4 mmol) 2-(1-tert.-butoxycarbonyl-2,5-dihydro-1H-pyrrol-3-yl-methyl)-malonic acid idimethylester n 140 ml DMF were added 1.94 g (108 mmol) water and 1.26 g( 21.6 mmol) sodium chloride. The mixture was degassed and heated to 150° C. for 30 h under an atmosphere of argon. After this period of time no starting material could be detected by TLC. The mixture was cooled to room temperature, diluted with 200 ml ether and washed three times with water, then with brine. The organic layer was dried over MgSO4 and evaporated. Purification by bulb-to-bulb distillation gave 3.38 g (92%) of 3-(2-methoxycarbonyl-ethyl)-2,5-dihydropyrrole-1-carboxylic acid tert. butylester as a colorless oil, b.p. 130° C. (0.2 mbar).

GC/MS (HP5890 II/HP 5972; column: HP 5,30 m×25 mm×0.25 (m film thickness, carrier gas: helium; temperature gradient: 50° C. 3 min; then with 20° C./min to 250° C.)

$t_R$=12.63 min m/z [%]=255 (M+, 0.2), 199 (48), 196 (2), 182 (10), 126 (26), 82 (54), 80 (32), 57 (100).

$^1$H-NMR (CDCl3, 300 MHz) δ=13.2, 13.2 [2s, 9H, C(CH3)3]*, 2.30–2.35, 2.40–2.44 (2m, 2H each, —CH2-CH2-), 3.58 (s,3H, OCH3), 3.91–4.00 (m, 4H 2-H, 5-H), 5.29–5.34 (m, 1H, 4-H) ppm.

$^{13}$C-NMR (CDCl3, 75 MHz) δ=23.7, 23.8 (t, 3-CH2)*, 28.2 [q, C(CH3)3], 31.7 (t, CH2COOMe), 51.4 (q, COOCH3), 52.8, 53.1, 54.4, 54.7 (4t, C-2, C-5)*, 78.9 [s, C(CH3)3], 118.9 (d, C-4), 137.8 (s, C-3), 153.9 (s, NCOO), 172.8 (s, COOCH3) ppm.

i) 3-[2,2,2-Trichlorethoxycarbonyl)-amino-ethyl]-2,5-dihydro-pyrrole-1-carboxylic acid tert. butyl ester To a solution of 3.57 g (14 mmol) 3-(2-methoxycarbonyl-ethyl)-2,5-dihydropyrrole-1-carboxylic acid tert. butyl ester in 45 ml THF/methanol/water 3:1:1 was added 1.18 g (28 mmol) LiOH(H2O and the mixture was stirred for 1 h at room temperature. The solution was diluted with water and washed three times with ethyl acetate. The aqueous layer was cooled in an ice bath and acidified with 1N hydrochloric acid against methyl orange. The turbid mixture was extracted three times with ether, the combined organic layers were dried over MgSO4 and evaporated to yield 3.41 g of a colorless solid, which turned dark on standing. The crude acid was dissolved in 140 ml dry toluene and 4.06 g (14 mmol) diphenyl phosphoryl azide and 1.47 g (14.5 mmol) triethylamine were added. The mixture was heated to 80° C. overnight. The solvent was removed in vacuo, the residual brown oil was dissolved in 20 ml THF and 3.14 g (21 mmol) 2,2,2-trichloroethanol and a small amount of cuprous chloride were added. The mixture was heated to reflux for 2 h, then the solvent was evaporated and the residue was purified by flash chromatography (petrol ether/ethyl acetate 3:1 to 2:1) to yield 4.31 g (79%) 3-[2-(2,2,2-trichlorethoxycarbonyl)-amino-ethyl]-2,5-dihydro-pyrrole-1-carboxylic acid tert. butyl ester as a colorless solid, m.p. 97°–98° C.

$^1$H-NMR (CDCl3, 200 MHz) δ=1.41 [s, 9H, C(CH3)3], 2.31 (br. m, 2H, 3-CH2-), 3.29–3.39 (m, 2H, CH2NH), 4.67 (br. m, 4H, 2-H, 5-H), 4.67 (s, 2H, CH2CCl3), 5.43 (br. m, 1H, 4-H) ppm.

$^{13}$C-NMR (CDCl3, 50 MHz) δ=28.6 [q, C(CH3)3], 29.2 (t, —CH2-CH2-NH), 39.2 (t, —CH2—CH2-NH), 53.2, 53.4, 54.6, 54.9, (4t, C-2, C-5), 74.5 (d, CH2CCl3), 79.5 [s, C(CH3)3], 95.8 (s, CH2CCl3), 120.8, 121.0 (2d, C-4), 136.3 (s, C-3), 154.2, 154.6 (2s, NCOO) ppm.

j) 3-[2-(2,2,2-Trichlorethoxycarbonyl)-amino-ethyl]-2,5-dihydropyrrole-1-(N,N'-di-tert.-butoxycarbonyl) carboxamidine To an ice-cooled solution of 1.936 g (5 mmol) 3-[2-(2,2, 2-trichlorethoxycarbonyl)-amino-ethyl]-2,5-dihydropyrrole-1-carboxylic acid tert. butyl ester in 10 ml dry dioxane was added 10 ml 4N hydrogen chloride in dioxane. The mixture was allowed to stand at 4° C. for 16 h. The solvent was then evaporated in vacuo without heating and then evacuated in high vacuum. The residue was suspended in 20 ml dry acetonitrile and 711 mg (5.5 mmol) ethyldi-isopropylamine followed by 1.614 mg (5.2 mmol) N,N'-bis-tert.-butyloxycarbonyl-1H-pyrazole-1-carboxamidine were added. The clear solution was stirred for 2 h at room temperature, then the solvent was distilled off and the residue was purified by flash chromatography (petrol ether/ethyl acetate 3:1 to 2:1) to yield 2.234 g (84%) of a colorless solid, m.p. 121°–123° C.

$^1$H-NMR (CDCl3, 200 MHz) δ=1.43 [s, 18H, C(CH3)3], 2.27–2.33 (br. m, 2H, 3-CH2-), 3.28–3.38 (m,2H, CH2NH). 4.31 (br. m, 4H, 2-H, 5-H), 4.65 (s, 2H, CH2CCl3), 5.47 (br. m, 1H, 4-H) pm.

$^{13}$C-NMR (CDCl3, 50 MHz) δ=28.0, 28.1 [2q, C(CH3)3], 29.0 (t, 3-CH2), 39.0 (t, CH2NH2), 55.4, 56.0 (2 br. t, C-2,

C-5), 74.5 (d, CH2CCl3), 79.5, 82.0 [2s, C(CH3)3], 95.6 (s, CH2CCl3), 119.9 (d, C-4), 135.3 (s, C-3), 150.4, 154.0, 154.5, 162.5 (4s, NCOO, N=C—N) ppm.

k)3-(2-Amino-ethyl)-2,5-dihydropyrrole-1-(N,N'-di-tert.-butoxycarbonyl)carboxamidine To a solution of 2.234 g (4.22 mmol) 3-[2-(2,2,2-trichlorethoxycarbonyl)-amino-ethyl]-2,5-dihydropyrrole-1-(N,N'-di-tert.-butoxycarbonyl) carboxamidine in 20 ml glacial acetic acid was added 1.31 g (40 g-atom) activated zinc and the mixture was stirred at room temperature for 2 h. Methanol was added, the mixture was filtered through celite, washed thoroughly with methanol and the filtrate was concentrated in vacuo. The residue was dissolved in water and made strongly alkaline with solid sodium hydroxide. The aqueous layer was extracted three times with ether, the combined organic layers were dried over MgSO4 and evaporated to yield 622 mg (41%) 3-(2-amino-ethyl)-2,5-dihydropyrrole-1-(N,N'-di-tert.-butoxycarbonyl) carboxamidine as a slightly yellow, amorphous solid.

$^1$H-NMR (CDCl3, 300 MHz) δ=1.45 [s, 18H, C(CH3)3], 2.21–2.26, (m, 2H, 3-CH2-), 2.83 (t, J=6.9 Hz, 2H, —CH2-NH2), 4.28–4.34 (br. m, 4H, 2-H, 5-H), 5.46 (br. s, 1H, 4-H) ppm.

$^{13}$C-NMR (CDCl3, 75 MHz) δ=27.85, 27.94 [2q, C(CH3)3], 32.2 (t, 3-CH2), 39.5 (t, CH2NH2), 55.2 56.7 (2t, C-2, C-5), ca 81 [br. s, C(CH3)3], 119.0 (d, C-4), 136.1 (s, C-3), 153.7 (s, NCOO) ppm.

1) HOOC-CH2-D-Cha-N-cyclopentyl)-Gly-Adc

A mixture of 0.41 g (0.81 mmol) N-(tert.butyloxycarbonyl)-N-(tert.butyloxycarbonyl-methyl)-(D)-cyclohexylalanyl-N-cyclopentylglycine, 0.15 ml (0.9 mmol) diisopropylmethylamine, and 0.29 g (0.9 mmol) TBTU in 25 ml dry DMF was stirred at room temperature for 30 min. Then 0.3 g (0.85 mmol) (3-(2-amino-ethyl)-2,5-dihydropyrrole-(1-(N,N'-di-tert.butoxycarbonyl)-carboxamidine was added and stirred for 70 h. The solvent was removed i.vac., water was added and extracted with ethyl acetate. The ethyl acetate was separated, washed with 1M hydrochloric acid and 5% aqueous sodium bicarbonate and dried over sodium sulfate. Filtration and removal of the solvent i. vac. produced 0.35 g (51%) N-(2-{[1-(N,N'-di-tert.butoxycarbonyl)-carboxamidino]-2,5-dihydro-pyrrol-3-yl}-ethyl)-[N-(tert.butyloxycarbonyl)-N-(tert.butyloxycarbonyl-methyl)-D-cyclohexylalanyl-(N-cyclopentylglycin)]amide as a colorless oil. FAB-MS: m/z 847 MH$^+$.

A solution of the above product (0.35 g, 0.41 mmol) in 10 ml 4N hydrogen chloride in dioxane was stored for 24 h at 5° C. The solvent was removed i.vac, and the oily residue was triturated with diethyl ether to yield the title compound as hydochloride quantitatively.

FAB-MS: m/z 491 MH$^+$.

$^1$H-NMR (d$_6$-DMSO, 250MHz): δ=0.8–4.8 ppm (m, broad), 5.68 (s, 1).

EXAMPLE 4

N-Me-D-Phe-Pro-Adc

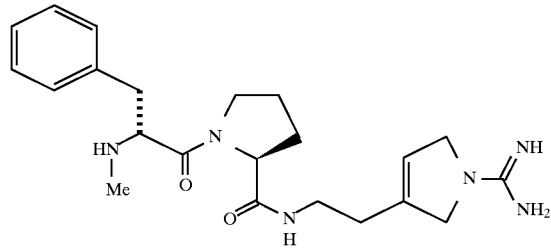

The title compound was synthesized as hydrochloride from Boc-N-Me-D-Phe-ProOH (Bajusz et al., J. Med. Chem. 1990, 33, 1729–1735) and 3-(2-amino-ethyl)-2,5-dihydropyrrole-1-(N,N'-di-tert.-butoxycarbonyl) carboxamidine (example 3 k) by the same method as described in example 31). FAB-MS: m/z 412 MH$^+$.

EXAMPLE 5

HOOC-CH2-D-Cha-Pro-Adc

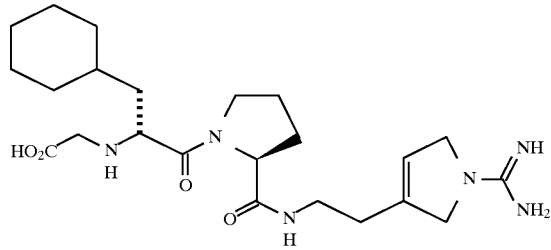

The title compound was synthesized as hydrochloride from N-(tert.-butyloxycarbonyl-methyl) -N-Boc-D-Cha-ProOH and 3-(2-amino-ethyl)-2,5-dihydro-pyrrole-1-(N,N'-di-tert.-butoxycarbonyl) carboxamidine (example 3 k) by the same method as described in example 31). FAB-MS: m/z 463 MH$^+$.

EXAMPLE 6

1-{3-[2-(1-amidino-2,5-dihydro-1H-pyrrol-3-yl)-ethyl]-2-oxo-oxazolidin-5-yl-methyl}-piperidine-4-carboxylic acid (a) A mixture of 3.1 g piperidine-4-carboxylic acid ethyl ester, 6.4 ml epichlorohydrin and 0.1 g tetrabutyl-ammonium bromide in 15 ml toluene and 15 ml concentrated sodium hydroxide solution was stirred for 4 h at room temperature and subsequently admixed with 50 ml water. The organic phase was separated, the aqueous phase was shaken three times with 20 ml methylene chloride each time, the combined organic phases were dried over sodium sulfate and the solvent was removed in a vacuum. 2.1 g (rac)-1-oxiran-2-ylmethyl-piperidine-4-carboxylic acid ethyl ester was obtained. EI-MS: m/z 213 M$^+$.

(b) A solution of 3 g of the amine prepared in example 3 k) and 1.73 g of the oxirane produced in 7a) in 20 ml ethanol was heated for 48 h under reflux. Subsequently the ethanol was removed in a vacuum and the residue was purified by column chromatography on silica gel (ethyl acetate/saturated methanolic ammonia 85/15). 1.5 g 1-{3-[2-(1-(N, N'-di-tert.-butoxy carbonyl)carboxamidino-2,5-dihydro-1H- pyrrol-3-yl)-ethylamino]-2-hydroxy-propyl }-piperidine-4-carboxylic acid ethyl ester was obtained in this way.

(c) A solution of 0.5 g of the aminoalcohol 7b) and 0.4 g carbonyldiimidazole in 5 ml dimethylformamide was stirred for 24 h at room temperature. Subsequently the reaction solution was concentrated to dryness by evaporation and the residue was purified by means of preparative HPLC (Merck, Select B, methanol/buffer (pH=7.5) 65/35). 0.35 g 1-{3-[2-(1-(N,N'-di-tert. -butoxycarbonyl)carboxamidino-2,5-dihydro-1H-pyrrol-3-yl)-ethylamino]-2-hydroxy-propyl}-piperidine-4-carboxylic acid ethyl ester was obtained in this manner.

(d) A solution of 0.35 g of the ethyl ester 6c) and 2 ml 1N sodium hydroxide solution in 5 ml methanol was stirred for 1 h at room temperature. Subsequently the methanol was removed in a vacuum and the residue was treated with 4M Hcl in dioxane for 3 hours at room temperature. Then the solvent was removed until drying in vacuo. 0.2 g of the title compound was obtained as hydrochlioride. FAB-MS: m/z366 [MH$^+$].

EXAMPLE 7

Troc-Ada-Gly-Asp-Ser a) 3-(2-Benzhydrilideneamino-2-ethoxycarbonyl-ethyl)-2,5-dihydropyrrole-1-carboxylic acid tert.-butylester To a solution of lithium hexamethyldisilazide, freshly prepared at 0° C. from 1.77 g (11 mmol) hexamethyldisilazane in 10 ml THF and 4.80 g (11 mmol) n-Butyl-lithium, (2.29 mmol/g in hexanes) and cooled to −78° C. was dropwise added a solution of 3.06 g (11 mmol) ethyl N-(diphenylmethylene)-glycinate in 10 ml THF. The deep orange enolate solution was stirred at this temperature for 30 min, then a solution of 2.41 g (10 mmol) 3-acetoxymethyl-2,5-dihydro-pyrrole-1-carboxylic acid tert.-butylester from example 3f) and 426 mg (0.4 mmol) Pd(PPh3)4 in 10 ml THF was added dropwise. The mixture was allowed to warm to room temperature overnight and was then diluted with ether and quenched by addition of sat. sodium bicarbonate. The aqueous layer was extracted with ether, the combined organic layers were washed with brine, dried over MgSO4 and evaporated. Flash chromatography of the residual oil (elution with petrol ether/ethyl acetate 3:1+1% triethylamine) gave 3.91 g (81%) 3-(2-benzhydrilidene-amino-2-ethoxycarbonyl-ethyl)-2,5-dihydropyrrole-1-carboxylic acid tert.-butylester as a slightly yellow oil.

$^1$H-NMR (CDCl3, 300 MHz) δ=1.27 (t, J=7.1 Hz, 3H, OCH2CH3),1.43 [s, 9H, C(CH3)3], 2.66–2.76 (m, 2H, 3-CH2-), 3.73–3.99 ( m, 1H, CH—N), 4.04–4.09 (br. m, 4H, 2-H, 5-H), 4.17 (q, J=7.1 Hz, 2H, OCH2CH3), 5.42 (br. m, 1H, 4-H), 7.11–7.81 (m, 10 H, Ar—H) ppm.

$^{13}$C-NMR (CDCl3, 75 Mhz) δ=14.2 (q, OCH2CH3), 28.5 [q, C(CH3)3], 33.1 (t, 3-CH2), 52.9, 55.1 (2t, C-2, C-5), 61.1 (t, OCH2CH3), 63.9 (d, CH—NH2), 79.1 [s, C(CH3)3], 121.9 (d, C-4), 127.7, 128.1, 128.3, 128.4, 128.5, 128.7 (6d, Ar—CH), 135.7, 135.8 (2s, Ar—C), 139.3 (s, C-3), 154.1 (s, NCOO), 170.8 (s, N=CPh2), 171.2 (s, OCOCH2CH3) ppm.

b) 3-(2-Amino-2-ethoxycarbonyl-ethyl)-2,5-dihydropyrrole-1-carboxylic acid tert.-butylester To 25 ml of a 0.5M solution of methoxylamine hydrochloride in 80% ethanol was added a solution of 448 mg (1mmol) 3-(2-benzhydrilideneamino-2-ethoxycarbonyl-ethyl)-2,5-dihydropyrrole-1-carboxylic acid tert.-butylester in 5 ml chloroform. After 5 min TLC analysis indicated the complete consumption of the starting material. The mixture was stirred for additional 30 min and then evaporated to dryness. The residue was dissolved in water and washed twice with ether. The aqueous layer was made alkaline by addition of 1N potassium hydroxide and extracted three times with ether. The combined organic extracts were dried over MgSO4 and evaporated to yield 214 mg (75%) 3-(2-amino-2-ethoxycarbonyl-ethyl)-2,5-dihydropyrrole-1-carboxylic acid tert.-butylester as a colorless oil which was pure according to GC.

GC/MS (HP 5890 II/HP 5972; column: HP 5,30 m×25 mm×0.25 (m film thickness, carrier gas: helium; temperature gradient: 50° C. 3 min; then with 20° C./min to 250° C.)

t$_R$=13.84 min m/z [%]=227 (M+-C4H9, <1), 211 (7), 182 (10), 155 (11), 137 (6), 126 (56), 108 (18), 94 (23), 82 (100), 74 (20), 57 (92).

$^1$H-NMR (CDCl3, 300 MHz) δ=1.23 (t, J=7.1 Hz, 3H, OCH2CH3), 1.42 [s, 9H, C(CH3)3], 2.35 (dd, 2J=14.2 Hz, 3J=8 Hz, 1H, CHaHbCHNH2), 2.50–2.55 (m, 1H, CHaHbCHNH2), 3.54 (dd, 3J=8, 5.5 Hz, 1H, CHNH2), 4.02–4.11 (br. m, 4H, 2-H, 5-H), 4.13 (q, J=7.1 Hz, 2H, OCH2CH3), 5.51 (br. m, 1H, 4-H) ppm.

$^{13}$C-NMR (CDCl3, 75 MHz) δ=14.1 (q, OCH2CH3), 28.5 [q, C(CH3)3], 34.5 (t, 3-CH2), 52.9 (d, CH—NH2), 53.0, 54.8 (2t, C-2, C-5), 61.0 (t, OCH2CH3), 79.3 [s, C(CH3)3], 122.2 (d, C-4) 135.5 (s, C-3), 154.1 (s, NCOO), 175.0 (s, OCOCH2CH3) ppm.

c)3-[2-(2,2,2-Trichloroethoxycarbonyl-amino)-2-ethoxycarbonyl-ethyl]-2,5-di-hydro-pyrrole-1-carboxylic acid tert.-butylester To an ice-cooled solution of 214 mg (0.75 mmol) 3-(2-amino-2-ethoxycarbonyl-ethyl)-2,5-dihydropyrrole-1-carboxylic acid tert.-butylester and 119 mg (1.5 mmol) pyridine in 2 ml methylene chloride was added a small amount of DMAP followed by 212 mg (1mmol) 2,2,2-trichloroethoxycarbonyl chloride. The mixture was allowed to warm to room temperature overnight. The mixture was diluted with ether, washed with water, sat. CuSO4, water and brine, dried over MgSO4 and evaporated. Purification of the residue by flash-chromatography (elution with petrol ether/ethyl acetate 3:1) gave 320 mg (93%) 3 -[2-(2,2,2-trichloroethoxycarbonyl-amino)-2-ethoxycarbonyl-ethyl]-2,5-dihydropyrrole-1-carboxylic acid tert.-butylester as a colorless oil, which was immediately used for the next step.

d)3-[2-(2,2,2-Trichloroethoxycarbonyl-amino)-2-ethoxycarbonyl-ethyl]-2,5-di-hydropyrrole-1-(N,N'-di-tert.-butoxycarbonyl) carboxamidine To an ice-cooled solution of 320 mg (0.67 mmol) 3-[2-(2,2,2-trichloroethoxy-carbonyl-amino)-2-ethoxycarbonyl-ethyl]-2,5-dihydropyrrole-1-carboxylic acid tert.-butylester in 1.5 ml dry dioxane was added 1.5 ml 4N hydrogen chloride in dioxane. The mixture was allowed to stand at 4° C. for 16 h. The solvent was then evaporated in vacuo without heating. The residue was suspended in 4 ml dry acetonitrile and 217 mg (0.7 mmol) ethyldiisopropylamine followed by 97 mg (0.75 mmol) N,N'-bis-tert.-butyloxycarbonyl-1H-pyrazole-1-carboxamidine were added. The resulting clear solution was stirred for 2 h at room temperature, then the solvent was distilled off and the residue was purified by flash chromatography (petrol ether/ethyl acetate 3:1 to 2:1) to yield 380 mg (94%) of a colorless foam.

$^1$H-NMR (CDCl3, 200 MHz) δ=1.21 (t, J=7.0 Hz, 3H, OCH2CH3), 1.43 [s, 9H, C(CH3)3], 2.53–2.64 (m, 2H, CH2CHNH), 4.16 (q, J 7.0 Hz, 2H, OCH2CH3), 4.29 (br. m, 4H, 2-H, 5-H), 4.67 s, 2H, CH2CCl3), 5.52–5.61 (m, 3H, —CHNH, 4-H) ppm.

$^{13}$C-NMR (CDCl3, 50 MHz) δ=14.1 (q, OCH2CH3), 28.0, 28.2 [2q, C(CH3)3], 31.8 (t, 3-CH2), 52.9 (d,

CH—NH2), 55.4, 57.1 (2br. t, C-2, C-5), 61.9 (t, OCH2CH3), 74.7 (t, CH2CCl3), 79.5, 83.5 [2s, C(CH3)3], 95.3 (s, CH2CCl3), 121.9 (d, C-4), 133.3 (s, C-3), 154.0 (s,NCOO), 171.1 (s, COOEt) ppm. (BOC—NCOO— and amidine —N—C═N-signals not visible due to line broadening).

e) 3-[2-(2,2,2-Trichloroethoxycarbonyl-amino)-2-carboxy-ethyl]-2,5-dihydropyrrole-1-(N,N'-di-tert.-butoxycarbonyl) carboxamidine To a solution of 219 mg (0.36 mmol) 3-[2-(2,2,2-trichloroethoxy-carbonyl-amino)-2-ethoxycarbonyl-ethyl]-2,5-dihydropyrrole-1-(N,N'-di-tert.-butoxycarbonyl) carbox-amidine in 4 ml THF/methanol/water3:1:1 was added 30 mg (0.72 mmol) LiOH*H2O. After stirring for 1 h at room temperature no starting material could be detected by TLC. The mixture was diluted with water, acidified by addition of 1N hydrogen chloride and extracted three times with ethyl acetate. The combined organic extracts were dried over MgSO4 and evaporated. The residue was purified by flash-chromatography (elution with ether +1% acetic acid) to yield 156 mg (76%) 3-[2-(2,2,2-trichloroethoxycarbonyl-amino)-2-carboxy-ethyl]-2,5-dihydropyrrole-1-(N,N'-di-tert.-butoxycarbonyl) carboxamidine (Troc-Ada(Boc2)-OH) as a colorless amorphous solid.

$^1$H-NMR (CDCl3, 250 MHz) δ=1.42 [s, 18H, C(CH3)3], 2.58–2.79 (br. m, 2H, CH2CHNH), 4.30–4.38 (m, 4H, 2-H, 5-H), 4.58 (d, 3=12.2 Hz, 1H, CHaHbCCl3), 4.75 (d, J=12.2 Hz, 1H, CHaHbCCl3), 5.53 (br. s, 1H, CHNH, 5.99 (br. m, 1H, 4-H) ppm.

f) Troc-Ada-Gly-Asp-Ser

The title compound was synthesized by solid-phase methodology on a SyRo II multiple peptide synthesizer (MultiSynTech, Bochum) on a 0.03 mmol scale using Fmoc-Ser(t-Bu)-trityl-polystyrene(1%)divinylbenzene resin (Fmoc-L-Ser(t-Bu)-TCP; loading: 0.57 mmol/g; PepChem, Tübingen) as starting material. The α-amino groups of the proteinogenic amino acids Gly and Asp were protected by 9-fluorenylmethoxycarbonyl (Fmoc), the side chain carboxy group of Asp by tert.-butyl. The non-proteinogenic amino acid Ada was used as Troc-Ada(Boc2)-OH (from example 8e). The Fmoc-protected amino acids were coupled in a 6-fold excess for 30 min in DMF. TBTU (1eq) and NNM (1 eq) were used as activating reagents. Cleavage of the Fmoc group was carried out in piperidine/dimethylformamide (1:1 v/v) for 2×10 min. Coupling of Troc-Ada(Boc2)-OH was performed manually in DMF within 1 h by using 0.048 mmol of the protected amino acid (1.65-fold excess) and equimolare amounts of TBTU and NMM for activation. The peptide was cleaved from the resin with 750 ul of acetic acid/trifluoroethanol/dichloromethane (30:10:70) within 2 h. After washing five times with 150 ul of the same solvent mixture the filtrates were combined, diluted with 10 ml heptane and concentrated. This procedure was repeated twice in order to remove the acetic acid completely. The oily residue was dissolved in 5 ml 4N hydrogen chloride in dioxane. To this solution 270 ul ethanedithiol were added and the mixture was stirred for 3 h at room temperature. Then the solvent was removed and the residue dissolved in heptane and concentrated again several times until the ethanedithiol was almost completely removed. The crude peptide was lyophilized from tert.-butanol/water (1:1) and yielded 15 mg of Troc-Ada-Gly-Asp-Ser.HCl as white lyophilisate.

Amino acid analysis: Gly 1.09(1); Asp 1.00(1); Ser 0.95 (1); peptide content: 69.9%

ESI-MS: m/z 631.1M$^+$.

EXAMPLE 8

Troc-Ada-Gly-Asp-Trp

The title peptide was prepared in the same manner as example 7f) starting from 50mg (0.03 mmol) Fmoc-L-Trp-TCP resin. 16 mg of Troc-Ada-Gly-Asp-Trp.HCl were obtained as white lyophilisate.

Amino acid analysis: Gly 1.19 (1); Asp 0.88 (1); Trp 1.00 (1); peptide content: 61.2%

ESI-MS: m/z 730.2M$^+$.

EXAMPLE 9

Troc-Ada-Gly-Asp-Phe

The title peptide was prepared in the same manner as example 7f) starting from 50 mg (0.03 mmol) Fmoc-L-Phe-TCP resin. 14 mg of Troc-Ada-Gly-Asp-Phe.HCl were obtained as white lyophilisate.

Amino acid analysis: Gly 1.08 (1); Asp 1.00 (1); Phe 0.93 (1); peptide content: 65.0% pos. LSIMS: m/z 692.1 MH$^+$.

The Troc protecting group of the compounds of example 7 to 9 can be removed by standard chemical reactions.

EXAMPLE 10

Ada-Gly-Asp-Tyr a)3-Acetoxymethyl-2,5-dihydro-pyrrole--(N,N∩-di-tert.butoxycarbonyl)carboxamidine To an ice-cooled solution of 1.21 g (5 mmol) 3-acetoxymethyl-2,5-dihydro-pyrrole-1-carboxylic acid tert.-butylester from example 3f) in 10 ml dry dioxane was added 10 ml 4N hydrogen chloride in dioxane. The mixture was stirred at 0° C. for 16 h. The mixture was evaporated to dryness without heating and then evacuated in high vacuum for several hours. The dark residue was suspended in 20 ml dry acetonitrile and 776 mg (6 mmol) ethyl diisopropylamine, followed by 1.71 g (5.5 mmol) N,N'-bis-tert.-butyloxycarbonyl-1H-pyrazole-1-carboxamidine were added. The mixture was stirred for 2 h at room temperature and then evaporated and purified by flash chromatography (petrol ether/ethyl acetate 3:1 to 2:1) to yield 1.87 g (97%) of 3-acetoxymethyl-2,5-dihydro-pyrrole-1-(N,N'-di-tert.-butoxycarbonyl) carboxamidine as a colorless, sticky solid.

$^1$H-NMR (CDCl3, 300 MHz) δ=1.45 (s, 18H, 2 t-Bu), 2.03 (s, 3H, OAc), 4.38 (br. m, 4H, 2-H, 5-H), 4.61 (s, 2H, CH2OAc), 5.72 (br. m, 1H, 4-H), 10.22 (br. s, 1H, NH) ppm.

$^{13}$C-NMR (CDCl3, 75 MHz) δ=20.4 (q, OOCCH3), 27.7, 27.9 [2q, C(CH3)3], 55.0 (br. t, C-2, C-5), 60.2 (t, CH2OAc), 79.3, 81.8 [2 br. s, C(CH3)3], 122.4 (d, C-4), 133.5 (s, C-3), 150 (br. s, NCOO), 153.9 (s, NC═N), 162 (br. s, NCOO), 170.2 (s, OOCH2CH3) ppm.

b) 3-(2-Benzhydrilideneamino-2-ethoxycarbonyl-ethyl)-2,5-dihydropyrrole-1-(N,N'-di-tert.-butoxycarbonyl) carboxamidine To a solution of lithium hexamethyldisilazide, freshly prepared at 0° C. from 710 mg (4.4 mmol) hexamethyldisilazane in 8 ml THF and 1.92 g (4.4 mmol) n-Butyl-lithium, (2.29 mmol/g in hexanes) and cooled to −78 ° C. was added a solution of 1.069 g (4 mmol) ethyl N-(diphenylmethylene)-glycinate in 8 ml THF. The orange enolate solution was stirred for 30 min at −78 ° C., then a solution of 1.039 g (3.7 mmol) 3-acetoxymethyl-2,5-dihydro-pyrrole-1-(N,N'-di-tert.-butoxycarbonyl) carboxamidine and 426 mg (0.4 mmol) Pd(PPh3)4 in 12 ml THF was added dropwise. The reaction mixture was allowed to warm to room temperature over 2 h and was stirred for additional 12 h. The mixture was diluted with ether and quenched by addition of sat. NaHCO3. The organic layer was washed with sat. NaHCO3 and brine, dried over MgSO4 and evaporated. Purification by flash chromatography (ethyl acetate/petrol ether 1:5+1% triethylamine) gave 1.03 g (47%) of 3-(2-benzhydrylideneamino-2-ethoxycarbonyl-ethyl)-2,5-dihydropyrrole 1-(N,N'-di-tert.-butoxycarbonyl) carboxamidine as a colorless, amorphous solid.

$^1$H-NMR (CDCl3, 300 MHz) δ=1.23 (t, J=7.1 Hz, 3H, OCH2CH3), 1.46 [br. s, 18H, C(CH3)3], 2.68 (br.m, 2H, 3-CH2-), 3.96 (br. m, 1H, CH—N), 4.15 (q, J=7.1 Hz, 2H, OCH2CH3), 4.16 4.29 (br. m, 4H, 2-H, 5-H), 5.41 (br. m, 1H, 4-H), 7.07–7.60 (m, 10 H, Ar—H) ppm.

$^{13}$C-NMR (CDCl3, 75 MHz) δ=13.9 (q, OCH2CH3), 28.0 [q, C(CH3)3], 32.5 (t, 3-CH2), 55.2, 56.9 (2t, C-2, C-5), 60.9 (t, OCH2CH3), 63.6 (d, CH—NH2), 79, 81.6 [2 br. s, C(CH3)3], 120.7 (d, C-4), 127.5, 127.8, 128.4, 128.5, 128.6, 130.2 (6d, Ar—CH), 134.8 (s, C-3), 135.8, 139.1 (2s, Ar—C), 150 (br. s, NCOO), 153.7 (s, NC=N), 162 (br. s, NCOO), 170.7 (s, N=CPh2), 171.2 (s, OOCH2CH3) ppm.

c) 3-(2-Amino-2-ethoxycarbonyl-ethyl)-2,5-dihydropyrrole-1-(N,N'-di-tert.-butoxycarbonyl) carboxamidine To a solution of 118 mg (0.2 mmol) 3-(2-benzhydrilideneamino-2-ethoxycarbonyl-ethyl)-2,5-dihydropyrrole-1-(N,N'-di-tert.-butoxycarbonyl) carboxamidine in 2 ml THF was added 1 ml 1N hydrochloric acid. The mixture was stirred at room temperature for 30 min. Water (5 ml) was added, the aqueous layer was separated and washed twice with ether. The aqueous layer was brought to pH=8.5 by addition of 1N NaHCO3 and was extracted five times with ether. The combined ether layers were washed with brine, dried over MgSO4 and evaporated. The residue was purified by flash chromatography (chloroform/methanol 20:1) to yield 79 mg (93%) 3-(2-amino-2-ethoxycarbonyl-ethyl)-2,5-dihydropyrrole-1-(N,N'-di-tert.-butoxycarbonyl) carboxamidine as a colorless oil.

$^1$H-NMR (CDCl3, 300 MHz) δ=1.22 (t, J=7.1 Hz, 3H, OCH2CH3), 1.45 [s, 18H, C(CH3)3], 2.33 (dd, 2J=16.6 Hz, 3J=8.1 Hz, 1H, CHaHbCHNH2), 2.54 (dd, 2J=16.6 Hz,3J=5.3 Hz, 1H, CHaHbCHNH2), 3.54 (dd,3J=8.1, 5.3 Hz, 1H, CHaHbCHNH2), 4.13 (q, J=7.1 Hz, 2H, OCH2CH3), 4.33 (br. m, 4H, 2-H, 5-H), 5.53 (br. m, 1H, 4-H) ppm $^{13}$C-NMR (CDCl3, 75 MHz) δ=13.9 (q, OCH2CH3), 27.9 [q, C(CH3)3], 34.1 (t, 3-CH2), 52.7 (d, CHNH2), 55.3, 56.9 (2d, C-2, C-5), 61.1 (t, OCH2CH3), ca 80 [2 br. s, C(CH3)3], 120.7 (d, C-4), 134.6 (s, C-3), 153.8 (s, NC=N), 174.6 (s, OOCH2CH3) ppm.

d) 3-(2-tert.-Butoxycarbonyl-amino-2-ethoxycarbonyl-ethyl)-2,5-dihydropyrrole-1-(N,N'-di-tert.-butoxycarbonyl) carboxamidine To a solution of 79 mg (0.19 mmol) 3-(2-amino-2-ethoxycarbonyl-ethyl)-2,5-dihydropyrrole-1-(N,N∩-di-tert.-butoxycarbonyl) carboxamidine in 1 ml dry acetonitrile was added 40 mg (0.3 mmol) ethyl diisopropylamine and 65 mg (0.3 mmol) di-tert.-butyl dicarbonate (Boc2O) and the mixture was stirred for 16 h at room temperature. The solvent was evaporated and the residue was purified by flash chromatography (petrol ether/ethyl acetate 2:1) to yield 83 mg (76%) 3-(2-tert.-butoxycarbonyl-amino-2-ethoxycarbonyl-ethyl)-2,5-dihydropyrrole-1-(N,N'-di-tert.-butoxycarbonyl) carboxamidine as a colorless oil.

$^1$H-NMR (CDCl3, 200 MHz) δ=1.22 (t, J=7.1 Hz, 3H, OCH2CH3),1.42, 1.47, 1.48 [3 s, 9H each, C(CH3], 2.41–2.66 (br. m, 2H, 3-CH2-), 4.17 (q, J=7.1 Hz, 2H, OCH2CH3), 4.32 (br. m, 4H, 2-H, m 5-H), 5.02 (br. m, 1H, CHNH), 5.52 (br. s, 1H, 4-H) ppm.

$^{13}$C-NMR (CDCl3, 50 MHz) δ=14.1 (q, OCH2CH3), 28.1, 28.3, 28.5 [3q, C(CH3)3], 31.8 (t, 3-CH2), 48.3 (d, CHNH), 52.0, 55.3 (2t, C-2, C-5),61.6 (t, OCH2CH3),121.3 (d, C-4),133.5 (s, C-3) 153.9 (s, N=C—N), 171.8 (s, COOEt) ppm. NCOO—, C(CH3)3 -signals not visible due to line broadening.

e) 3-(2-tert.-Butoxycarbonyl-amino-2-carboxy-ethyl)-2,5-dihydropyrrole-1-(N,N'-di-tert-butoxycarbonyl) carboxamidine To a solution of 267 mg (0.63 mmol) 3-(2-tert.-butoxycarbonyl-amino-2-ethoxycarbonyl-ethyl)-2,5-dihydropyrrole-1-(N,N'-di-tert.-butoxycarbonyl) carboxamidine in 5 ml THF/methanol/water 3:1:1 was added 50 mg (1.2 mmol) LiOH.H2O. After 30 min stirring at room temperature no starting material could be detected by TLC. The mixture was made acidic by addition of 1N HCl, diluted with water and extracted three times with ether. The combined organic extracts were washed with brine, dried over MgSO4 and evaporated. The residue was purified by flash-chromatography to give 98 mg (31%/o) of 3-(2-tert.-Butoxycarbonyl-amino-2-carboxy-ethyl)-2,5-dihydropyrrole-1-(N,N'-di-tert.-butoxycarbonyl ) carboxamidine (Boc-Ada(Boc2)-OH) as a colorless amorphous solid.

$^1$H-NMR (CDCl3, 300 MHz) δ=1.39, 1.44 [2s, 9H, 18H, C(CH3)3], 2.49–2.67 (br. m, 2H, 3-CH2-), 4.33 (br. m, 4H, 2-H, 5-H), 5.30 (br. d, 1H, CHNH), 5.56 (br. s, 1H, 4-H) ppm.

$^{13}$C-NMR (CDCl3, 75 MHz) δ=27.7, 28.9, 28.0 [3q, C(CH3)3], 31.3 (t, 3-CH2), 52.0 (d, CHNH), 55.3, 56.9 (2t, C-2, C-5), 80.0, 80.9 [2s, (C(CH3)3], 121.1 (d, C-4), 133.6 (s, C-3), 153.2 (s, N=C—N), 155.2 (br. s, NCOO), 176.5 (s, COOH) ppm.

f) Ada-Gly-Asp-Tyr

The title peptide was prepared in same manner as example 8f) staring from 50 mg (0.03 mmol) Fmoc-L-Tyr-TCP resin. Instead of Troc-Ada(Boc2)-OH Boc-Ada(Boc2)-OH from example 12e) was used for the N-terminal amino acid. 12 mg of Ada-Gly-Asp-Tyr. HCl were obtained as white lyophilisate.

Amino acid analysis: Gly 1.05 (1); Asp 0.96 (1); Tyr 1.00 (1); peptide content: 61.1% pos. LSIMS: m/z 534.3 MH$^+$.

EXAMPLE 11

Ada-Gly-Asp-Phe-NH2

The title compound was synthesized by solid-phase methodology on a ACT90 automated peptide synthesizer (Advanced ChemTec, Louisville, Ky.) using tritylchloride-polystyrene(1%)divinylbenzene (TCP; loading: 0.96 mmol/g; PepChem, Tübingen) and Fmoc-Asp-Phe-NH2 (NovaBiochem, Läufelfingen) as starting materials. The Fmoc-protected dipeptide amide (320.4 mg; 0.72 mmol) was dissolved in 4 ml dichloromethane. After 1 eq N-methyl-morpholin (NM1) was added the solution was given to 444 mg (0.48 mmol) dry TCP resin. After 5 min an additional volume of 130 ul NNM was added yielding a total amount of 1.80 mmol NMM in solution. The mixture was shaken for further 60 min. Then the residual tritylchloride groups were capped by the addition of 0.5 ml methanol. After further 20 min the resin was filtered off and washed with dichloromethane, DMF and methanol. The resin was dried under reduced pressure. Loading of the resin was determined to be 0.057 mmol/g. The Fmoc group was removed by treatment with piperidine/dimethylformamide (1:1 v/v) for 2×10 min. Afterwards Fmoc-Gly-OH was coupled within 30 min in 30-fold excess in a double coupling procedure using 1 eq TBTU and 1 eq NMM as activing agents. After removal of the Fmoc group by the same procedure as described above Boc-Ada(Boc2)-OH was coupled manually in DMF within 17 h by using a 2.5-fold excess of the protected amino acid and equimolar amounts of TBTU and NMM for activation. Cleavage from the resin and deprotection of the peptide was performed according to example 8f). Instead of heptane trifluoroethanol (2 ml) was used to dissolve the deprotected peptide. From this solution the crude peptide was precipitated by the addition of 16 ml diethylether. After centrifugation the supernatant was discarded and the precipitate lyophilized from tert.-butanol/water (1:1 v/v). Ada-Gly-Asp-Phe-NH2.HCl (28 mg) was obtained as white lyophilisate.

Amino acid analysis: Gly 1.05 (1); Asp 1.03 (1); Phe 0.97 (1); peptide content: 67.4% pos. LSIMS: m/z 502.3 M+.

EXAMPLE 12

DESCRIPTION OF THE PHARMACOLOGICAL EXPERIMENTS

Thrombin time

A common test in clinical coagulation diagnostics is the thrombin time. This parameter detects the action of thrombin on fibrinogen and the formation of blood clots. Inhibitors of thrombin result in an increased thrombin time.

In order to obtain plasma 9 parts fresh blood from healthy donors are mixed with one part sodium citrate solution (0.11 mol/l) and centrifuged at ca. 3000 rpm for 10 min at room temperature. The plasma was removed by pipette and can be stored for ca. 8 h at room temperature.

200 ul citrate plasma was incubated for 2 min at 37° C. in a sphere coagulometer (KC10 from the Amelung Company). 10 ul dimethylsulfoxide (DMSO) or a solution of the active substance in DMSO was added to 190 ul preheated thrombin reagent (Boehringer Mannheim, GmbH; contains ca. 3 U/ml horse thrombin and 0.0125M Ca2+). A stopwatch was started when this 200 ul solution was added to the plasma and the time point at which coagulation starts was determined. In the control measurements the thrombin time was ca. 24 seconds and was increased by the compound of example 1 depending on the concentration (test concentration/increase of thrombin time: 340 nM/>300* sec; 34 nM/ 65 sec; 3.5 nM 5 sec). [* the experiment was stopped after 5 minutes.]

Thrombin inhibition

The kinetic measurements were carried out in 0.1M phosphate buffer which contained 0.2M sodium chloride and 0.5% polyethylene glycol 6000 at a pH=7.5 and 25° C. using the substrate H-(D)-Phe-Pro-Arg-pNA (S-2238 Kabi) and human thrombin (Sigma, specific activity=2150 NIH units/mg) in polystyrene semimicro-cuvettes in a total volume of 1 ml.

In a preexperiment is was determined whether the compound of formula (I) inhibits thrombin rapidly or slowly. For this the reaction was started first by adding 0.03 NIH units thrombin to a 100 $\mu$M solution of the substrate and the active substance. In a second experiment substrate was added to a solution of thrombin and the active substance which had been incubated for 5 min. The increase of the concentration of p-nitro-anilide with time was monitored spectrophotometrically for 12 min at 405 nm (UV-VIS spectrophotometer Lambda-2 from the Perkin-Elmer Company). Since the measurement curves obtained in both experiments were linear and parallel, the active substance of formula (I) is a rapid thombin inhibitor. The inhibition constant Ki was determined as follows. The substrate was added at concentrations of 100 $\mu$M, 50 $\mu$M, 30 $\mu$M, 20 $\mu$M and at each substrate concentration a measurement was carried out without inhibitor and three measurements were carried out in the presence of various concentrations of the inhibitor of formula (I). The reactions were started by addition of thrombin. The increase in absorbance at 405 nm caused by the formation of p-nitroanilide was monitored for a time period of 12 min. Measurement points (time versus absorbance) were transferred to a PC at intervals of 20 sec. The rates Vo (changes in absorbance per see; measurements without inhibitor) and Vi (measurements with inhibitor) were determined from the data by linear regression. Only that part of each measurement was used in which the substrate concentration had been reduced by less than 15%. From one measurement series (constant inhibitor concentration, variable substrate concentrations) Km' and Vmax were determined by a non-linear fit to the equation $$V = \frac{Vmax * [S]}{[S] + Km'}.$$

Finally, Ki was determined from the total series of measurements by non-linear fit to the equation $$V = \frac{Vmax * [S]}{Km * (1 + [S]/Ki) + [S]}.$$

The Michaelis constant Km was 3.8±2 $\mu$M. The inhibition constant Ki of the compound of example 1 is 150 nM.

Inhibition of trypsin 10 mg bovine pancreatic trypsin (Sigma) was dissolved in 100 ml mM hydrochloric acid and stored in a refrigerator. 20 $\mu$l thereof was admixed with 980 $\mu$l 1 mM hydrochloric acid. 25 $\mu$l thereof was used for each measurement. The measurement was carried out as described for thrombin. Km=45 $\mu$M. The compound of example 1 inhibits trypsin with an inhibition constant Ki of 100 nM.

GpIIb/IIa inhibition

The GpIIb/IIIa fibrinogen Elisa is a modification of assays which are described in the following literature: Nachman, R. L. & Leung, L. L. K. (1982): J. Clin. Invest. 69: 263–269 and Wright, P. S. et al. (1993): Biochem. J. 293:263–267.

Microtiter plates were coated overnight with 2 $\mu$g/ml isolated activated GpIIb/IIIa receptor. After unbound receptor had been removed by washing several times the surface of the plates is blocked with 1% casein and it is washed again. The test substance is added at the required concentrations and the plates are incubated for 10 minutes while shaking. The natural ligand of the gpIIb/IIIa receptor, fibrinogen, is added. After incubating for 1 hour unbound fibrinogen is removed by washing several times and the bound fibrinogen is determined by means of a peroxidase-conjugated, anti-fibrinogen monoclonal antibody by measuring the optical density at 405 nm in an ELISA instrument. The inhibition of a fibrinogen-GpIIb/IIIa interaction results in a low optical density. The IC$_{50}$ value was determined by a concentration/effect curve.

| Compound | gpIIb/IIIa-Inhibition IC$_{50}$ [$\mu$M] |
| --- | --- |
| Example 7 | 14.4 |
| Example 8 | 0.4 |
| Example 9 | 2.3 |
| Example 10 | 2.4 |
| Example 11 | 12.8 |

We claim:

1. A compound of formula (I)

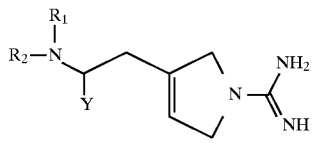

wherein $R_1$ and $R_2$ are independently selected from the group consisting of hydrogen, an amino acid, a peptidyl residue having 1–50 amino acids, alkylsulfonyl and arylsulfonyl, wherein aryl is a carbocycle having 6 to 14 carbon atoms or a heterocycle having 1 to 3 heteroatoms selected from the group consisting of O, N and S, Y is hydrogen or a group of formula COX, wherein X is selected from the group consisting of hydrogen, $OR_3$ and $NR_1R_2$, wherein $R_3$ is hydrogen or C1–C6 alkyl and $R_1$ and $R_2$ are as denoted above, or an optically active isomer or pharmacologically acceptable salt thereof.

2. A compound as claimed in claim 1, wherein the amino acid is selected from the group consisting of a naturally-occurring D-amino acid, citrulline, homocysteine, homoserine, hydroxyproline, hydroxylysine, ornithine, sarcosine, tranexamic acid, [3-(2-aminoethyl)-2,5 dihydropyrrol-1-yl]-carbamidine, (1-amidino-2,5-dihydro-1H-pyrrol-3-yl)-alanine, cyclohexyl-alanine, 2-carboxy-6-hydroxy-octahydroindol, 3-amino-2-oxo-hexahydro-1-azepine-acetic acid, 4-piperidine carboxylic acid, pipecolic acid, phenyllactic acid, N-methyl-phenylalanine, HOOCCH2-phenylalanine, HOOCCH2-cyclohexylalanine, 1-carboxy-perhydroiso-quinoline, N-cyclopentylglycine, EtSO2-phenylalanine and N-butyl-SO2-3-amino-2-oxo-hexahydro-1-azepine-acetic acid.

3. A pharmaceutical composition, comprising at least one compound as claimed in claim 1 and a pharmaceutically acceptable carrier.

4. A method of treating osteoporosis, inflammation or a disease which is due to a thromboembolic event in a patient in need thereof, comprising administering to the patient a disease treating-effective amount of a compound as claimed in claim 1.

5. The method as claimed in claim 4, wherein the disease which is due to a thromboembolic event is selected from the group consisting of stroke, myocardial infarction and an arterial occlusive disease.

6. The method as claimed in claim 4, wherein the compound is administered orally in a daily dose of 10–1500 mg per day per 75 kg body weight.

7. The method as claimed in claim 6, wherein the daily dose is divided into 2 to 3 individual doses.

8. The method as claimed in claim 4, wherein the compound is administered by injection in a daily dose of 50–2000 mg per day per 75 kg body weight.

9. The method as claimed in claim 8, wherein the daily dose is divided into 2 to 8 individual doses.

10. A compound of formula (I)

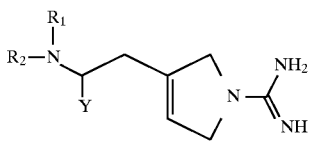

wherein $R_1$, $R_2$ and Y are each independently selected from the group consisting of:

(1) hydrogen;

(2) C1–C6 alkyl which is unsubstituted or substituted with phenyl which is unsubstituted or substituted with O—(C1–C6 alkyl) which is unsubstituted or substituted by a 5- or 6-membered heterocyclic ring having 1–2 heteroatoms and having 1–2 substituents which is unsubstituted or has 1–2 substituents each independently selected from the group consisting of =O and (C1–C6 alkyl)—C(=O)—OH;

(3) a 5- or 6-membered heterocyclic ring having 1–2 heteroatoms which is unsubstituted or substituted with (A) (C1–C6 alkyl)—C(=O)-phenyl which is unsubstituted or substituted in the phenyl with 1–2 O—(C1–C6 alkyl)—C(=O)—OH groups, or (B) a 5- or 6-membered heterocyclic ring having 1–2 heteroatoms which is unsubstituted or substituted with (C1–C6 alkyl)—C(=O)—OH;

(4) a 5- or 6- membered carbocyclic ring which is unsubstituted or substituted with (C1–C6 alkyl)—C(=O)—OH; and (5) —V—C(=O)—X where V is a chemical bond or C1–C6 alkyl and X is selected from the group consisting of (A) C1–C6 alkyl which is unsubstituted or substituted 1–2 times by (i) N(—$R_3$)—$R_4$, where $R_3$ and $R_4$ are each independently selected from the group consisting of hydrogen, a 5- or 6-membered carbocyclic ring and C(=O)—$R_5$ where $R_5$ is selected from the group consisting of (1) C1–C6 alkyl which is unsubstituted or has 1–2 substituents selected from the group consisting of phenyl, N(—H)—(C1–C6 alkyl) and N(—H)-(sulfonyl C1–C6 alkyl) and (2) a 1–2 ring heterocycle having 1–3 heteroatoms, or $R_3$ and $R_4$, together with the N atom to which they are attached, form a 5-7 membered heterocyclic ring which is unsubstituted or has 1–2 substituents each independently selected from the group consisting of =O, N(—H)—(C1–C6 alkyl) and N(—H)-(sulfonyl C1–C6 alkyl), (ii) C(=O)—N(—H)—(C1–C6 alkyl) where the alkyl is unsubstituted or has 1–3 substitutents each independently selected from the group consisting of C1–C6 alkyl, =O, —OH, phenyl, a 5- or 6-membered heterocyclic ring having 1–2 heteroatoms, and =CH, and (iii) a 5- or 6-membered carbocyclic ring, (B) a 5- or 6-membered heterocyclic ring having 1–2 heteroatoms and which is unsubstituted or has 1–2 C1–C6 alkyl substituents each of which is unsubstituted or substituted with 1–3 substituents each independently selected from the group consisting of =O, —OH, —O—CH3, a 5- or 6-membered carbocyclic ring, a 1–2 ringed heterocyclic ring having 1–3 heteroatoms and N(—H)—(C1–C6 allyl) where the alkyl is unsubstituted or has 1–2 substitutents each independently selected from =O, —OH, SO2 and 5- or 6-membered heterocyclic ring having 1–2 heteroatoms;

(C) phenyl which is unsubstituted or is substituted with —O—(C1–C6 alkyl) wherein the alkyl is unsubstituted or has 1–2 substituents each independently selected from the group consisting of =O and —OH, or the phenyl forms one ring of a bicyclic heterocycle containing 1–2 heteroatoms which is unsubstituted or has 1–3 substituents each independently selected from the group consisting of =O and C1–C6 alkyl which is unsubstituted or has 1–2 substituents selected from the group consisting of phenyl, =O and —OH; and (D) N(—H)—(C1–C6 alkyl) which is unsubstituted or substituted by 1–4 substituents each independently selected from the group consisting of =O, —OH and N(—H)—(C1–C6 alkyl) wherein the alkyl is unsubstituted or has 1–3 substituents each independently selected from the group consisting of phenyl, =O and —OH; or two of $R_1$, $R_2$ and Y, together with the N to which they are bound, form a 1–2 ring heterocycle with 0–1 additional heteroatoms, which is unsubstituted or substituted by 1–3 substituents independently selected from the group consisting of =O, C1–C6 alkyl wherein the allyl is unsubstituted or has 1–2 substituents each independently selected from the group consisting of (A) =O, (B) N(—H)—(C1–C6 alkyl) which is unsubstituted or substituted by 1–2 substituents each independently selected from the group consisting of =O and —OH, (C) —O— phenyl which is unsubstituted or substituted in the phenyl with C1–C6 alkyl which is unsubstituted or substituted by 1–2 substituents each independently selected from the group consisting of =O and —OH, (D) carbocycle which is unsubstituted or substituted with C1–C6 alkyl which is unsubstituted or substituted by 1–2 substituents each independently selected from the group consisting of =O and —OH, (E) C1–C6 alkyl which is unsubstituted or substituted with 1–2 substituents each independently selected from the group consisting of (i) =O, (ii) N(—H)—(C1–C6 alkyl) which is unsubstituted or substituted by 1–2 substituents each independently selected from the group consisting of =O and —OH and (iii) a 5- or 6-membered heterocyclic ring having 1–2 heteroatoms which is unsubstituted or substituted with C1–C6 alkyl which is unsubstituted or substituted by 1–2 substituents each independently selected from the group consisting of =O and —OH, and the third of $R_1$, $R_2$ and Y is selected from the group consisting of groups (1)–(5) as noted above.

11. A pharmaceutical composition, comprising at least one compound as claimed in claim 10 and a pharmaceutically acceptable carrier.

12. A method of treating osteoporosis, inflammation or a disease which is due to a thromboembolic event in a patient in need thereof, comprising administering to the patient a disease treating-effective amount of a compound as claimed in claim 10.

13. The method as claimed in claim 12, wherein the disease which is due to a thromboembolic event is selected from the group consisting of stroke, myocardial infarction and an arterial occlusive disease.

14. The method as claimed in claim 12, wherein the compound is administered orally in a daily dose of 10–1500 mg per day per 75 kg body weight.

15. The method as claimed in claim 14, wherein the daily dose is divided into 2 to 3 individual doses.

16. The method as claimed in claim 12, wherein the compound is administered by injection in a daily dose of 50–2000 mg per day per 75 kg body weight.

17. The method as claimed in claim 16, wherein the daily dose is divided into 2 to 8 individual doses.

* * * * *

UNITED STATES PATENT AND TRADEMARK OFFICE
CERTIFICATE OF CORRECTION

PATENT NO. : 5,856,309

DATED : January 5, 1999

INVENTOR(S) : Konetschny-Rapp et al.

It is certified that error appears in the above-identified patent and that said Letters Patent is hereby corrected as shown below:

On the title page, Item [30], please insert --,

Foreign Application Priority Data

```
Oct. 14, 1994    [DE] Germany..........P 44 36 772.4
Dec. 09, 1995    [DE] Germany............195 46 018.9
Apr. 11, 1996    [DE] Germany............196 14 179.6 --
```

Signed and Sealed this

Fourth Day of May, 1999

Attest:

Attesting Officer

Q. TODD DICKINSON

Acting Commissioner of Patents and Trademarks